United States Patent [19]
Zuk, Jr.

[11] Patent Number: 5,798,041
[45] Date of Patent: Aug. 25, 1998

[54] IN-LINE LIQUID FILTRATION DEVICE USEABLE FOR BLOOD, BLOOD PRODUCTS OR THE LIKE

[75] Inventor: Peter Zuk, Jr., Harvard, Mass.

[73] Assignee: Hemasure, Inc., Marlborough, Mass.

[21] Appl. No.: 524,049

[22] Filed: Sep. 6, 1995

[51] Int. Cl.$^6$ .................... B01D 29/00; B01D 29/05
[52] U.S. Cl. .................... 210/456; 210/435; 210/436; 210/472
[58] Field of Search .................... 210/346, 435, 210/436, 446, 450, 455, 486, 456, 472, 488, 490, 495, 499

[56] References Cited

U.S. PATENT DOCUMENTS

| | | | |
|---|---|---|---|
| 2,073,991 | 3/1937 | Koser | 210/456 |
| 2,665,009 | 1/1954 | Harstick | 210/456 |
| 2,784,843 | 3/1957 | Braunlich | 210/456 |
| 3,556,302 | 1/1971 | Agranat | 210/456 |
| 3,560,377 | 2/1971 | Loeffler | 210/456 |
| 3,631,654 | 1/1972 | Riely et al. | 210/446 |
| 3,935,110 | 1/1976 | Schmid et al. | 21/456 |
| 4,009,715 | 3/1977 | Forberg et al. | 210/455 |
| 4,038,191 | 7/1977 | Davis et al. | 210/456 |
| 4,113,627 | 9/1978 | Leason | 210/446 |
| 4,159,954 | 7/1979 | Gangemi | 210/489 |
| 4,170,056 | 10/1979 | Meyst et al. | 210/446 |
| 4,229,306 | 10/1980 | Hein et al. | 210/451 |
| 4,894,152 | 1/1990 | Colvin, Jr. et al. | 210/456 |
| 4,895,806 | 1/1990 | Le et al. | 435/293.1 |
| 4,925,572 | 5/1990 | Pall | 210/767 |
| 4,944,876 | 7/1990 | Miller | 210/456 |
| 5,126,045 | 6/1992 | Kohlheb et al. | 210/489 |
| 5,126,054 | 6/1992 | Matkovich | 21/436 |
| 5,143,630 | 9/1992 | Rolchigo | 210/456 |
| 5,171,439 | 12/1992 | Vakharia | 210/436 |
| 5,316,678 | 5/1994 | Heaslip | 210/486 |
| 5,429,742 | 7/1995 | Gutman et al. | 210/495 |
| 5,451,321 | 9/1995 | Matkovich | 210/641 |
| 5,454,951 | 10/1995 | Hoopman | 210/456 |
| 5,536,405 | 7/1996 | Myrna et al. | 210/346 |

*Primary Examiner*—John Kim
*Attorney, Agent, or Firm*—Heslin & Rothenberg, P.C.

[57] ABSTRACT

An in-line liquid filtration device useable for filtration of blood, blood products or the like includes a housing having an inlet port, an outlet port, at least one filter element disposed in the housing between the inlet port and outlet port so as to filter liquid which flows into the filtration device via the inlet port. The filter element divides the housing into a first chamber and a second chamber. The device allows gases to vent the filtration device through the outlet port. The means may include a flow deflector within the first chamber and/or the second chamber. The means may also include a channel, preferably spiral, within either the first chamber and/or second chamber. The filtration device allows air therein to be purged downstream into either an air collecting bag or into the blood receiving bag without the manipulation of the height of the filtration device or the blood receiving bag.

27 Claims, 33 Drawing Sheets

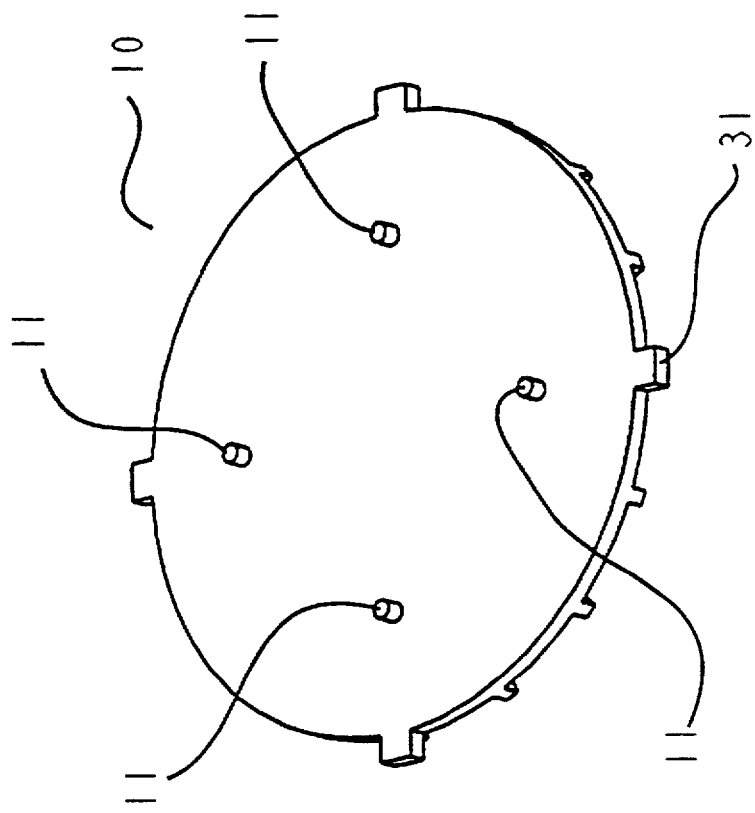
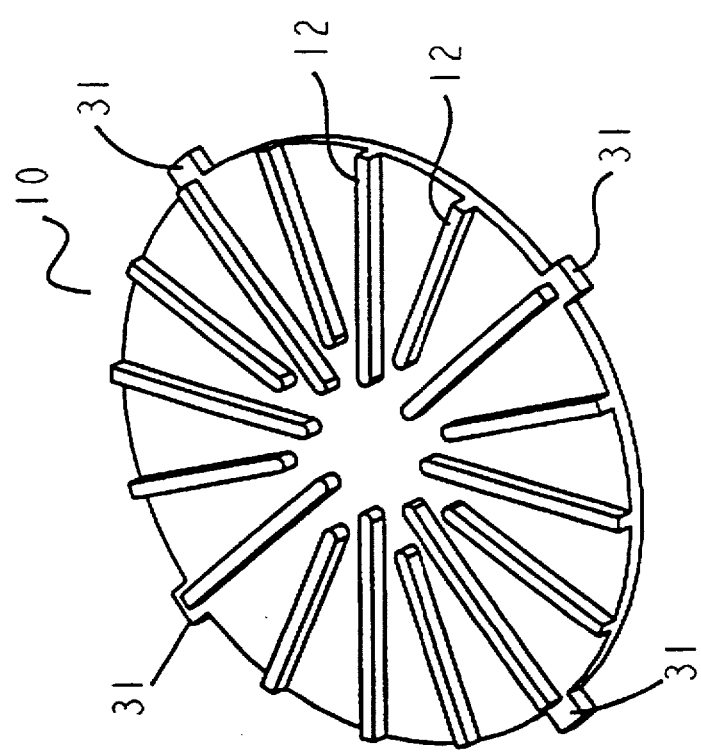
figure 3b
figure 3a

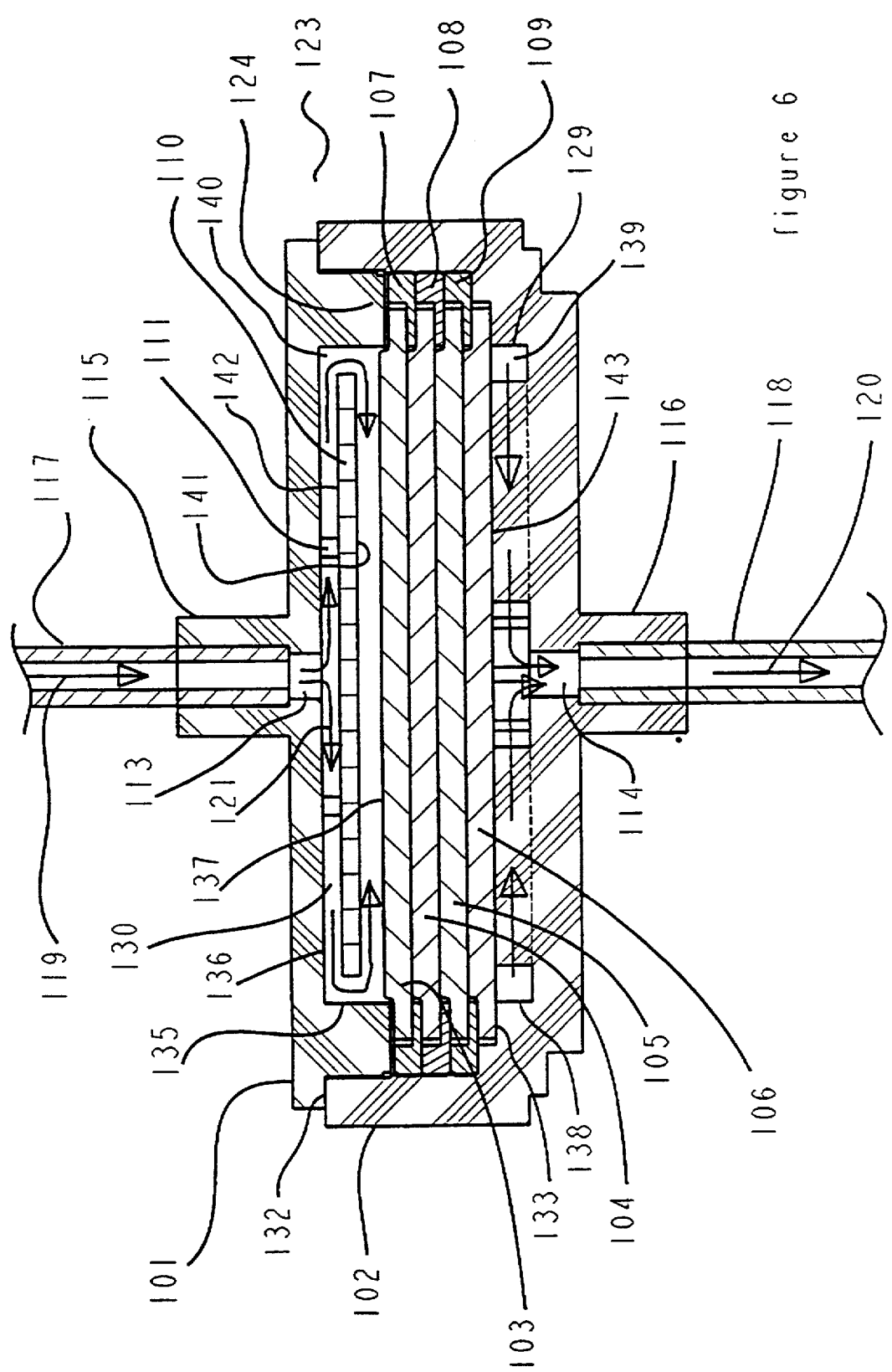

5,798,041

IN-LINE LIQUID FILTRATION DEVICE USEABLE FOR BLOOD, BLOOD PRODUCTS OR THE LIKE

FIELD OF THE INVENTION

This invention relates generally to liquid filtration devices. More particularly, this invention relates to an in-line gravity driven liquid filtration device usable to filter blood, blood products and to remove chemical agents used to disinfect or otherwise treat blood or blood products.

BACKGROUND OF THE INVENTION

Typically, gravity feed blood filtration devices require user manipulation of vent filters during the filtration process. The manipulation of the vent filters must occur at the proper time during the filtration process or the system will not filter properly and blood being filtered may be rendered unusable. Since, user manipulation of vent filters is time consuming and costly, it is desirable to achieve a liquid filtration device which may filter blood without the manipulation of vent filters or filtration devices. Moreover, blood filtration devices usually allow liquid to remain within the filtration device after filtration has occurred. This remaining liquid, referred to as a hold up volume, is often greater than the desired maximum amount. Also, blood filtration devices allow an undesirably high amount of air that is purged therefrom to be left in the receiving blood bag.

The filtration device disclosed in U.S. Ser. No. 08/209, 523, and entitled "A Filtration Device Usable for Removal of Leukocytes and Other Blood Components" filed Mar. 10, 1994 now U.S. Pat. No. 5,472,605, which is hereby incorporated by reference and made a part of the disclosure herein, overcomes the aforementioned vent filter manipulation problem. However, it is desirable to reduce the hold up volume of this device and to reduce the manufacturing cost thereof, while maintaining an acceptable total filtration time. It is also desirable to achieve a filtration device which does not require draining of the outlet tubing at the end of the filtration cycle.

Blood filtration devices typically do not have features which prevent the tubing attached thereto from becoming kinked. It is, therefore, desirable to achieve a liquid filtration device which filters blood without the manipulation of vent filters, minimizes hold up volume, that minimizes the volume of air that is added to the receiving blood bag, that reduces manufacturing cost and also reduces the possibility of kinked tubing when the device is assembled into a filtration system and packaged for shipping.

SUMMARY OF THE INVENTION

The shortcomings of the prior art may be alleviated using a filtration device constructed in accordance with the principles of the present invention. The filtration device of the present invention is capable of filtering blood to remove leukocytes, other blood components and chemical agents which may be used to treat the blood. The filtration device includes a first chamber capable of collecting and directing the flow of unfiltered liquid therein and a second chamber in fluid flow relationship with the first chamber capable of collecting and directing the flow of filtered liquid.

In one aspect of the invention, the in-line liquid filtration device comprises a housing having an inlet port and an outlet port therein, a filter element disposed within the housing between the inlet port and outlet port so as to filter the liquid which flows into the filtration device via the inlet port, and means within the filtration device, for allowing gases such as air to vent from filtration device through the outlet port during filtration. Between the inlet port and outlet port, the filter elements divide the housing into a first chamber and a second chamber. The filtration device may be sized so that the distance between a filter element and the inlet port prevents the accumulation of gases in the first chamber. Similarly, the liquid filtration device may be sized so that the distance between the at least one filter element and the outlet port forces gases within the second chamber to enter the outlet port during filtration.

In another aspect of the invention, the means, disposed within the device, for allowing gases to vent through the filtration device through the outlet port during filtration comprises a flow deflector disposed within the second chamber between the filter element and the outlet port. The flow deflector may comprise a relatively flat member such as a disk, and the disk may comprise at least one radially extending rib. The filtration device may comprise more than one filter element and a seal ring may be mounted between two of the filter elements. The inlet port and outlet port of the filtration device may be coaxially oriented. The housing may comprise an inlet section and an outlet section attached to the inlet section. The inlet port may be disposed within the inlet section and the outlet port may be disposed within the outlet section. The filter element may be sealed between the inlet section and either the outlet section or a seal ring. If the device contains a plurality of filter elements therein, the filter elements may be stacked on top of one another and separated about their periphery by seal rings.

In another aspect of the invention, the means, disposed within the filtration device, for allowing gases to vent from filtration device through the outlet port during filtration may comprise a flow deflector disposed within the first chamber between the filter element and the inlet port. The flow deflector may comprise a flat member such as a disk and the disk may be suspended within the first chamber.

In yet another aspect of the invention, the aforementioned means may comprise a channel disposed below the filter element in the second chamber, the channel being adapted to allow fluid to flow to the outlet port from the filter element. The channel may comprise a substantially spiral channel. The filter element may cover the channel to allow liquid filtered within the filter element to flow directly into the channel.

The aforementioned means may further comprise a second channel, the second channel being disposed within the first chamber and adapted to allow fluid to flow from the inlet port to the filter element. The second channel may cover the filter element wherein liquid within the second channel flows directly into the filter element. The second channel may comprise a spiral channel leading from an outer periphery of the first chamber to a central location within the first chamber. The second channel may also comprise a modified spiral channel. The filtration device may also comprise means for supporting the filter element within the filtration device. This means may comprise a screen or a molded part.

The filtration device may also comprise a third channel extending radially between the inlet port and the second channel. The inlet port may be located about a periphery of the housing and a second channel extending from the periphery of the first chamber within the housing to a central location within the first chamber. The inlet port may be adapted to receive flexible tubing therein and may include a tapered hole. The filtration device may also include a tube guide on the housing adapted to guide a flexible tube into the inlet port. The tube guide may also comprise a substantially right angle support member. At least one protruding rib may extend from an inside diameter of the tapered hole.

The device may also include a second outlet port being positioned within the housing at a location below the filter element to allow air within the housing to flow therethrough. The second outlet port may have a hydrophilic filter disposed to allow air to pass therethrough without allowing certain liquids to flow therethrough.

The filtration device may further comprise an in-line vent in fluid flow relationship with the outlet port. The in-line vent being adapted with a hydrophilic filter therein, an inlet, a first outlet and a second outlet. The hydrophilic filter may be located between the inlet and the first outlet and adapted to allow air to pass therethrough without allowing filtered liquid to pass therethrough.

BRIEF DESCRIPTION OF THE DRAWINGS

The invention may be best understood by reference to the detailed description of the preferred embodiments herein when read in conjunction with the drawings in which:

FIG. 3A depicts a top isometric view of the flow deflector used within the filtration device depicted in FIG. 1 and FIG. 2;

FIG. 3B depicts a bottom isometric view of the flow deflector used within the filtration device depicted in FIG. 1 and FIG. 2;

FIG. 6 depicts a sectional schematic representation the filtration device depicted in FIG. 5 showing the flow of fluid therein and usable in accordance with the principles of the present invention;

DETAILED DESCRIPTION OF THE PREFERRED EMBODIMENTS

As referred to herein, the terms upstream, top or up refers to a location of the flow of liquid prior to filtration through filter elements within the filtration device of the present invention. Conversely, the terms downstream, bottom or down as used herein refers to a location of the flow of liquid after filtration through filter elements within the filtration device of the present invention. Moreover, as used herein, the terms radially and axially refer to the radial and axial direction, respectively, relative to axis A—A (FIG. 2) running lengthwise through the center of the filtration device.

As disclosed herein, the filtration device of the present invention is preferably disk or cylindrically shaped and intended to be used for in-line filtration. The filtration device of the present invention may be used for the filtration of various liquids. However, it is particularly suited for the filtration of blood and/or blood products and will be described herein in reference to blood filtration.

Although various embodiments of the filtration device constructed in accordance with the present invention are disclosed herein, each embodiment enables air within the filtration device to vent downstream without manipulation of various components, the use of vent filters or other external means. Each embodiment of the filtration device comprises a housing typically formed by an inlet section, an outlet section, one or more filter elements, and means for allowing gases to vent from the filtration device through an outlet port.

Figure 1:
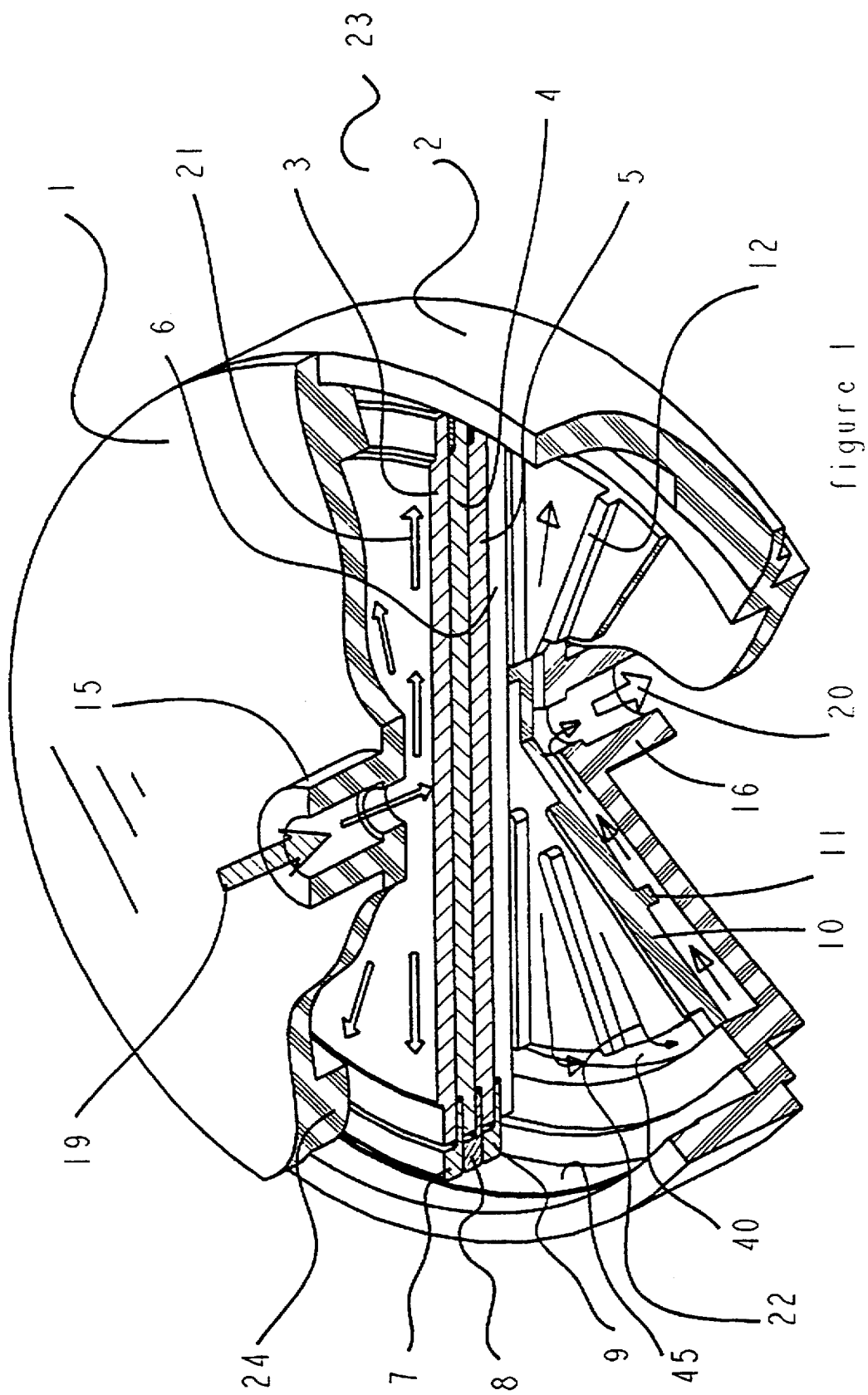
FIG. 1 depicts an isometric view with portions removed therefrom of a filtration device having a flow deflector in the second chamber thereof constructed in accordance with the principles of the present invention.
Figure 2:
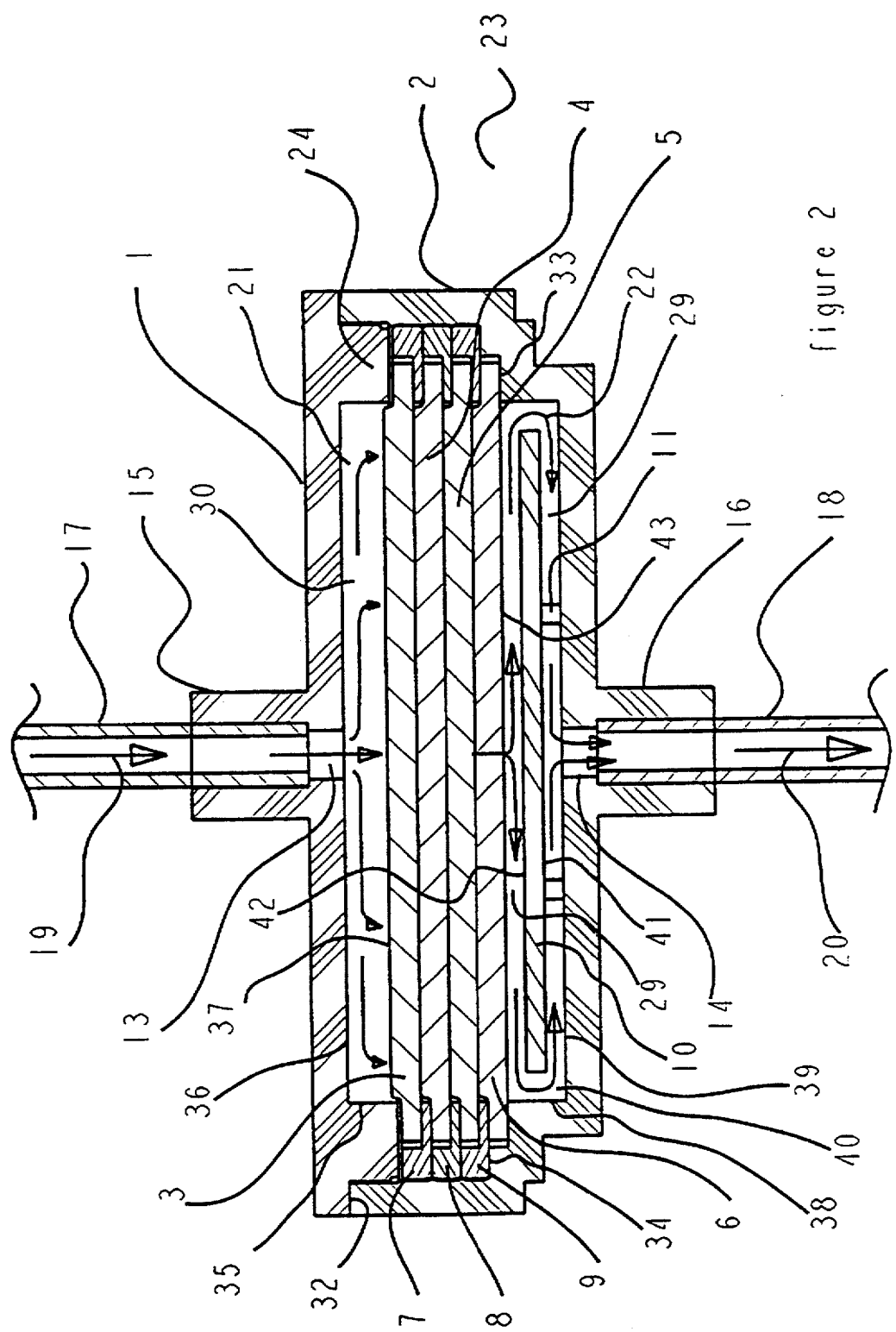
FIG. 2 depicts a sectional schematic representation of the filtration device of FIG. 1 depicting the flow of fluid therein and constructed and usable in accordance with the principles of the present invention.

One embodiment of the filtration device, shown in FIGS. 1 and 2, and constructed in accordance with the principles of the present invention incorporates a downstream flow deflector. The filtration device includes an inlet section 1 an outlet section 2, filter elements 3, 4, 5, 6, seal rings 7, 8, 9 and flow deflector 10. The filter elements are preferably made of a material which is capable of filtering blood as disclosed in U.S. patent application Ser. No. 08/209,523 filed on Mar. 10, 1994, now U.S. Pat. No. 5,472,605, and entitled "A Filtration Device Useable for Removal of Leukocytes and Other Blood Components."

Referring to FIGS. 1 and 2, the filtration device 23 consists of an inlet section 1 which is sealed to outlet section 2 at a joint 32 therebetween. Preferably the joint is sealed by ultrasonic weld, a heat weld, a solvent weld, a glue joint or any other means for creating a leak tight seal. A filter element 6 is sealed into the outlet section 2 by compression thereby forming a compression seal. The outer periphery of filter element 6 is compressed between shelf 33 of outlet section 2 and a seal ring 9. Filter element 5, located on top of filter element 6, is sealed into outlet section 2 using a compression seal. The outer periphery of filter element 5 is compressed between seal ring 8 and seal ring 9. Filter element 4, located on top of filter element 5, is sealed into outlet section 2 also using a compression seal. The outer periphery of filter element 4 is compressed between seal ring 7 and seal ring 8. Filter element 3, located on top of filter element 4, is also sealed into outlet half 2 using a compression seal. The outer periphery of filter element 3 is compressed between seal ring 7 and the seal rib 24 protruding in the axial direction along the outer perimeter of inlet section 1. Seal rings 7, 8 and 9 are preferably press fit with wall 45 of outlet section 2. However, seal rings 7, 8 and 9 may be bonded to or into outlet section 2 using an ultrasonic weld, heat weld, solvent weld, glue or by using any other sealing means which will create a leak tight seal. If the seal rings are not press fitted into outlet section 2, then seal ring 9 could be bonded to outlet section 2 and the bottom surface of seal ring 8 could be bonded to the top surface of seal ring 9 and the bottom surface of seal ring 7 could be bonded to the top surface of seal ring 8. Although the device illustrated in FIGS. 1 and 2 includes four filter elements, one or more filter elements may be used.

The cavity 21 formed within the interior of the device 23 by the inside walls of inlet section 1 and outlet section 2 is divided into two chambers by filter elements 3, 4, 5 and 6. The upstream, upper or first chamber 30 is formed by wall 35 of inlet section 1, wall 36 of inlet section 1 and the upper surface 37 of filter element 3. The downstream, lower or second chamber is formed by wall 38 of outlet section 2, wall 39 of outlet section 2 and the lower surface 43 of filter element 6. The lower chamber 29 is divided into two sections by a flow deflector 10 within the lower chamber. The first section of lower chamber 29 is bounded by bottom surface 43 of filter element 6 and top surface 42 of flow deflector 10. The second section of lower chamber 29 is bounded by bottom surface 41 of flow deflector 10 and by the surface 39 of outlet section 2.

Referring to FIGS. 3A and 3B, the flow deflector is formed of a thin disk which contains radial filter support ribs 12 on a first side thereof, alignment tabs 31 on the outer periphery, and support pins 11 on a second side thereof. The filter support ribs 12 function as a means for allowing radial flow of fluid along the first side of the flow deflector. However, other means for allowing such a flow such as a series of support pins or a woven screen may be used in lieu of support ribs 12. The support pins 11 function as a means for supporting the flow deflector 10 above wall 39 of outlet section 2. The alignment tabs function as a means for positioning the flow deflector 10 within the lower chamber 29.

Figure 4:
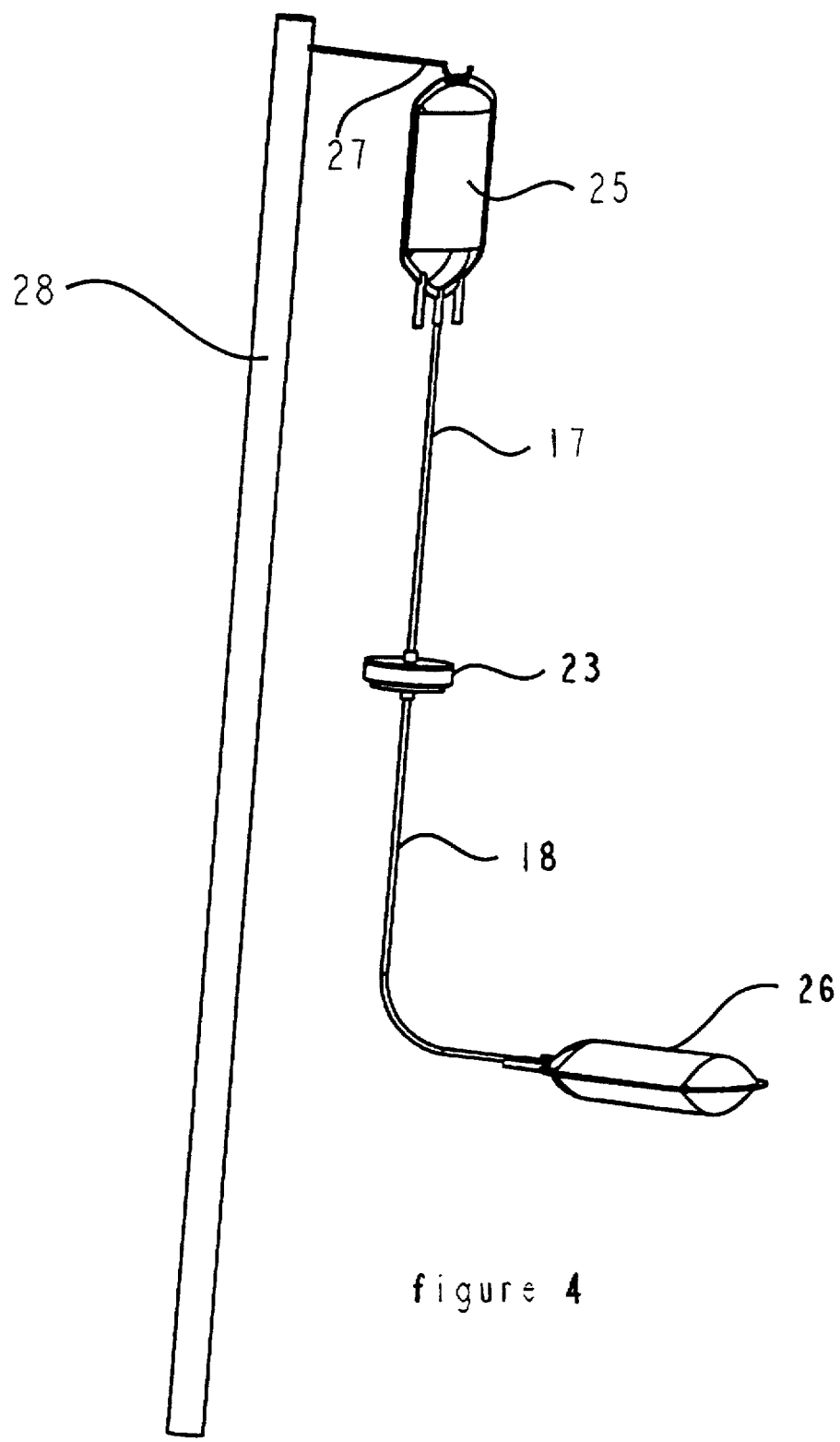
FIG. 4 depicts the filtration device depicted in FIG. 1 and FIG. 2 in an operational assembly with tubing, a blood supply bag and blood collecting bag.

In FIG. 4 the filtration device 23 depicted in FIG. 1 and FIG. 2 is in an operational assembly with inlet tube 17, outlet tube 18, feed blood bag 25 and receiving blood bag 26. Preferably, the user will purchase the assembly of FIG. 4 sterilized without feed blood bag 25 with the inlet end of inlet tube 17 sealed to maintain system sterility. For performing filtration, inlet tube 17 (FIG. 2) attached to tube socket 15 at the center of the inlet section 1 would be bonded to a pigtail on feed blood bag 25 using a sterile docking device as is well known in the art. Inlet tube 17 is in fluid flow relationship with upper chamber 30 via inlet port 13. Outlet tube 18, attached to, for example, a blood collection bag, is bonded to outlet tube socket 16 located at the center of the outlet section 2. Outlet tube 18 is in fluid flow relationship with bottom chamber 29 via outlet port 14.

Filtration device 23 hangs in line. Liquid, such as blood enters filtration apparatus 23 from its inlet port 13 and liquid exits the filtration apparatus 23 from its outlet port 14. In the process of filling the filtration device 23 with liquid all of the air therein before the filtration process began is purged out of filtration device 23 through outlet tube 18 into receiving blood bag 26 before liquid starts to flow out of filtration device 23. This process assures that little or no air gets trapped in filter elements 3, 4, 5 or 6. Therefore, the entire exposed surface area of the filter elements gets used for filtration.

When filtering blood, the user would first close inlet tube 17 near the end to be attached to the feed blood bag, with a tube clamp (not shown) and then make a sterile connection between the inlet end of inlet tube 17 and the feed blood bag 25 using a sterile docking device as is well known in the art. The actual sterile connection is made between inlet tube 17 and a short length of tube which is a part of feed blood bag 25. The resulting system is illustrated in FIG. 4. Feed blood bag 25 may be suspended from an appropriate mechanism such as pole 28 with hook 27. The receiving blood bag 26 may be suspended by the mechanism or may rest on a surface such as a bench top or the like.

Referring to FIGS. 1, 2 and 4, once the tube clamp (not shown) is opened blood will begin to flow from feed blood bag 25 through inlet tube 17, through inlet port 13, into upper chamber 30. The air that was in inlet tube 17 will be forced ahead of the blood flow into upper chamber 30. Blood enters upper chamber 30 in the center thereof. Therefore, upper chamber 30 will fill with blood from the center first, then radially outward. This radial flow is illustrated by arrows in FIGS. 1 and 2. Because upper chamber 30 fills from the center radially outward, the filter elements 3, 4, 5, 6 will wet from the center radially outward. As upper chamber 30 fills from its center radially outward the air in upper chamber 30 will be forced through the non wet portions of filter elements 3, 4, 5 and 6 into lower chamber 29, through outlet port 14, through outlet tube 18, into the receiving blood bag 26. The upper chamber 30 should be sized in relation to the initial blood flow rate to assure that all of the air initially in upper chamber 30 will be forced through filter elements 3, 4, 5 and 6. If the volume of the upper chamber 30 in relation to initial blood flow rate is too large, some air will be trapped in upper chamber 30.

As the filter elements wet radially outward, the air that was in the filter elements will be forced into lower chamber 29, through outlet port 14, through outlet tube 18, into receiving blood bag 26. Because the filter elements wet from the center radially outward, blood will first flow out of filter element 6 from its center and then continue to flow out of filter element 6 in a radially outward pattern. Therefore, the first section of lower chamber 29 will fill from its center radially outward. As the first section of lower chamber 29 fills radially outward all of the air that was in filter elements 3, 4, 5 and 6 will be forced radially outward through the first section of lower chamber 29.

Once the first section of lower chamber 29 is filled with blood the blood will flow into the second section of lower chamber 29 radially inward forcing air into the outlet port thereby venting air downstream. Once the second section of lower chamber 29 is filled with blood outlet port 14 and outlet tube 18 will fill with blood. Finally, the receiving blood bag 26 will begin to fill with blood. The flow around the flow deflector is illustrated by arrows in FIG. 2.

Figure 5:
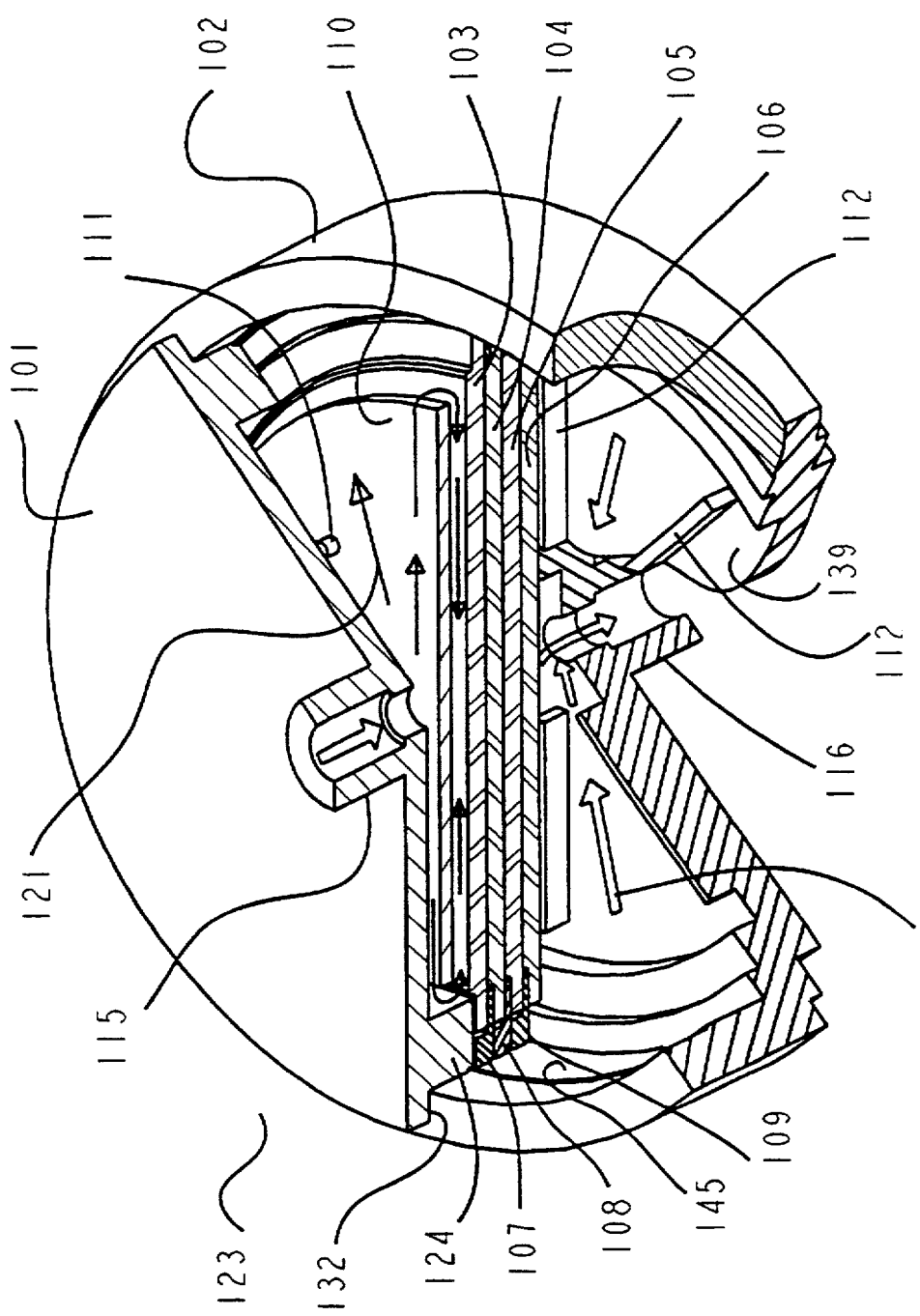
FIG. 5 depicts an isometric view of a filtration device having a flow deflector in the first chamber and having portions removed therefrom, constructed in accordance with the principles of the present invention.

A second embodiment of the filtration apparatus having a top flow deflector constructed in accordance with the principles of the present invention is shown in FIGS. 5 through 8. Referring to FIGS. 5 and 6, the filtration device 123 includes an inlet section 101 which is sealed to outlet section 102 at a joint 132 therebetween. Preferably, the joint is sealed by an ultrasonic weld, a heat weld, a solvent weld, a glue joint or any other means for creating a leak tight seal. A filter element 106 is sealed into the outlet section 102 by compression thereby forming a compression seal. The outer periphery of filter element 106 is compressed between shelf 133 of outlet section 102 and a seal ring 109. Filter element 105, located on top of filter element 106, is sealed into outlet section 102 using a compression seal. The outer periphery of filter element 105 is compressed between seal ring 108 and seal ring 109. Filter element 104 located on top of filter element 105, is sealed into outlet section 102 by compression thereby forming a compression seal. The outer periphery of filter element 104 is compressed between seal ring 107 and seal ring 108. Filter element 103, located on top of filter element 104, is sealed into outlet section 102 by compression thereby forming a compression seal. The outer periphery of filter element 103 is compressed between seal ring 107 and seal rib 124 protruding in the axial direction along the outer perimeter of inlet section 101. Seal rings 107, 108, 109 are preferably press fit with the wall 145 of outlet section 102. However, seal rings 107, 108 and 109 may be bonded to or into outlet section 102 using an ultrasonic weld, heat weld, solvent weld, glue or by using any other sealing means which will create a leak tight seal. If the seal rings are not press fitted into outlet section 102, then seal ring 109 could be bonded to outlet section 102 and the bottom surface of seal ring 108 could be bonded to the top surface of seal ring 109 and the bottom surface of seal ring 107 could be bonded to the top surface of seal ring 108. Although the device illustrated in FIGS. 5 and 6 contains four filter elements, any number of filter elements may be used.

The cavity formed by the inside walls of inlet section 101 and outlet section 102 is divided into two chambers by filter elements 103, 104, 105 and 106. The upper chamber 130 is formed by wall 135 of inlet section 101, wall 136 of inlet section 101 and the upper surface 137 of filter element 103. The lower chamber 129 is formed by a side wall 138 of the outlet section 102, a lower surface 139 of outlet section 102 and the lower surface 143 of filter element 106. The upper chamber is divided into two sections by flow deflector 110.

Figure 7B:
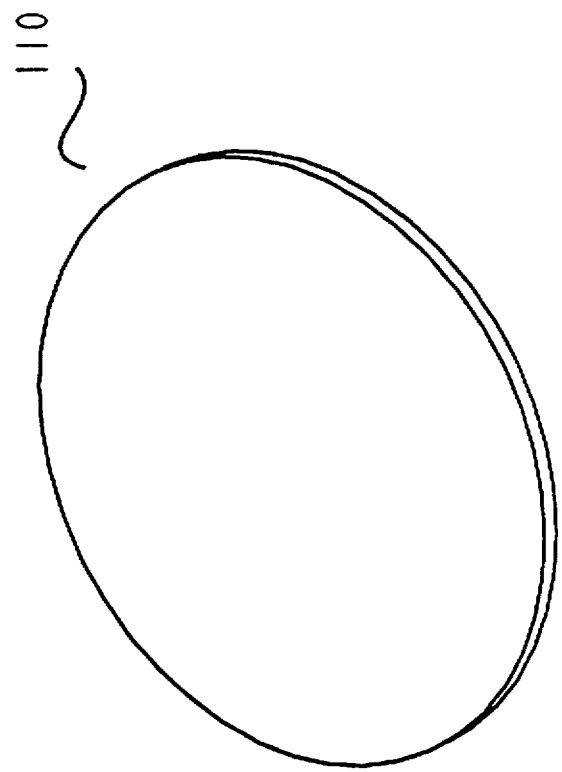
FIG. 7B depicts a bottom isometric view of the flow deflector used within the filtration device in FIG. 5 and FIG. 6.
Figure 7A:
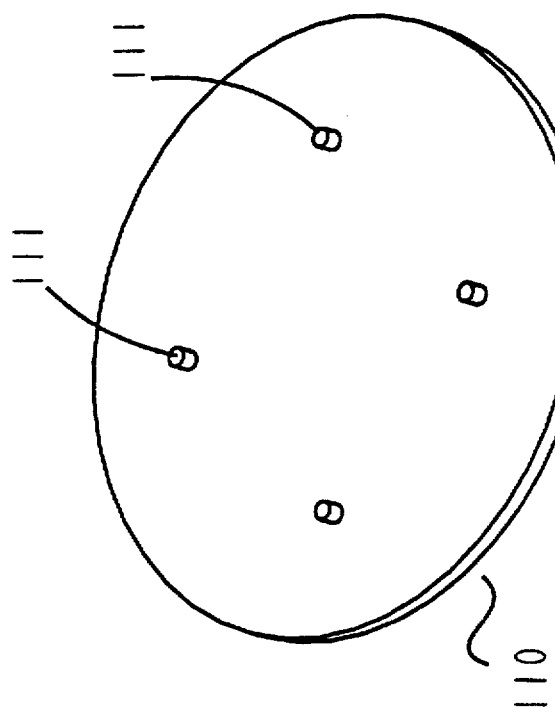
FIG. 7A depicts a top isometric view of the flow deflector used within the filtration device depicted in FIG. 5 and FIG. 6.

Referring to FIGS. 7A and 7B flow deflector 110 includes a thin disk having suspension pins 111 thereon. The suspension pins 111 are bonded to inlet section 101 to allow the flow deflector 110 to be centered in upper chamber 130. Upper chamber 130 is, therefore, divided into two sections, a top or first section and a bottom or second section. The top section of upper chamber 120 is bounded by the interior surface 136 of inlet half 101 and by the top surface 142 of flow deflector 110. The bottom section of upper chamber 130 is bounded by the bottom surface 141 of flow deflector 110 and by the top surface 137 of filter element 103.

For performing filtration, inlet tube 117, attached to for example a blood supply bag, is bonded to tube socket 115 of the inlet section 101. Inlet tube 117 is in fluid flow relationship with upper chamber 130 via inlet port 113. Outlet tube 118 is bonded to outlet tube socket 116 of the outlet section 102 and is attached to at its other end, for example, a blood collection bag. Outlet tube 118 is in fluid flow relationship with bottom chamber 129 via outlet port 114.

The filtration device 123 is used in the same manner previously discussed in reference to the embodiment of the filtration device 23 shown in FIGS. 1 and 2, and is placed in operational assembly in the same manner as depicted in FIG.

4. The filtration device 123 hangs in line. Liquid such as blood enters the filtration device 123 from its inlet port 113 and liquid exits the filtration device 123 from its outlet port 114. In the process of filling the filtration device 123 with fluid such as blood, all of the air in the filtration device 123 (before filtration begins) is purged therefrom through outlet tube 118 into receiving blood bag 126 before liquid starts to flow out of the filtration device. Therefore, little or no air is trapped in filter elements 103, 104, 105 or 106, and the exposed surface area of the filter elements is used for filtration. When filtering blood the user would first close inlet tube 117 near the end of inlet tube 117 with a tube clamp (not shown) and then make a sterile connection between the inlet end of inlet tube 117 and a feed blood bag (not shown) using a sterile docking device known in the art. The actual sterile connection is made between inlet tube 117 and a short length of tube which is a part of a feed blood bag. A feed blood bag may be suspended from an appropriate mechanism such as pole with hook. The receiving blood bag may be suspended by the mechanism or may rest on a surface such as a bench top or the like.

Referring to FIGS. 5 and 6, once the filtration device 123 is placed in an operational assembly, a tube clamp on the inlet tube 117, (not shown), is opened and blood will begin to flow from a feed blood bag (not shown) through inlet tube 117, through inlet port 113, into upper chamber 130. The air that was in inlet tube 117 will be forced ahead of the blood flow into upper chamber 130. Blood enters upper chamber 130 and the first section of upper chamber 130 will fill from the center radially outward. This radial flow is illustrated by arrows in FIGS. 5 and 6. The gap between surface 136 of inlet section 101 and the top surface 142 of flow deflector 101 should be sized in relation to the initial blood flow so that all of the air therein is purged from the gap as it fills from its center radially outward with blood. Once the first section of upper chamber 130 is filled with blood, blood will spill over flow deflector 110 through gap 140 and then begin to fill the second section of upper chamber 130 from its outer periphery radially inward. The gap between bottom surface 141 of flow deflector 110 and the top surface 137 of filter element 103 should be sized in relation to the initial blood flow so that all of the air in the gap is purged therefrom as the gap fills from its outer periphery radially inward with blood. The blood flow rate into the second section of the upper chamber 130 must be sufficient to force the air from the second section through the filter elements. If the blood flow rate is insufficient, it must either be increased and/or the flow deflector moved more towards the filter elements.

Because the lower portion of upper chamber 130 fills from its outer periphery radially inward filter elements 103, 104, 105 and 106 will wet from their outer periphery radially inward. As the filter elements wet, any air therein will be forced into lower chamber 129 and then through outlet port 114, through outlet tube 118 into the receiving blood bag. Outlet section 102 contains filter support ribs 112 which provide support for the filter elements and also allows radial flow into lower chamber 129. However, any filter support means that allows for radial flow in lower chamber 129 can be used in place of filter support ribs 112. Because filter elements 103, 104, 105 and 106 wet from their outer periphery radially inward, lower chamber 129 will fill from its outer periphery radially inward.

The height of lower chamber 129, as defined by the lower surface 143 of filter element 106 and the inner surface 139 of the outlet section 102, should be made small enough in relation to initial blood flow so that all of the air that is purged from filter elements 103, 104, 105 and 106 (as they wet with blood) is purged from lower chamber 129. Once lower chamber 129 is filled with blood, outlet port 114 and then outlet tube 118 will fill with blood. Finally, the receiving blood bag will begin to fill with blood.

Figure 8:
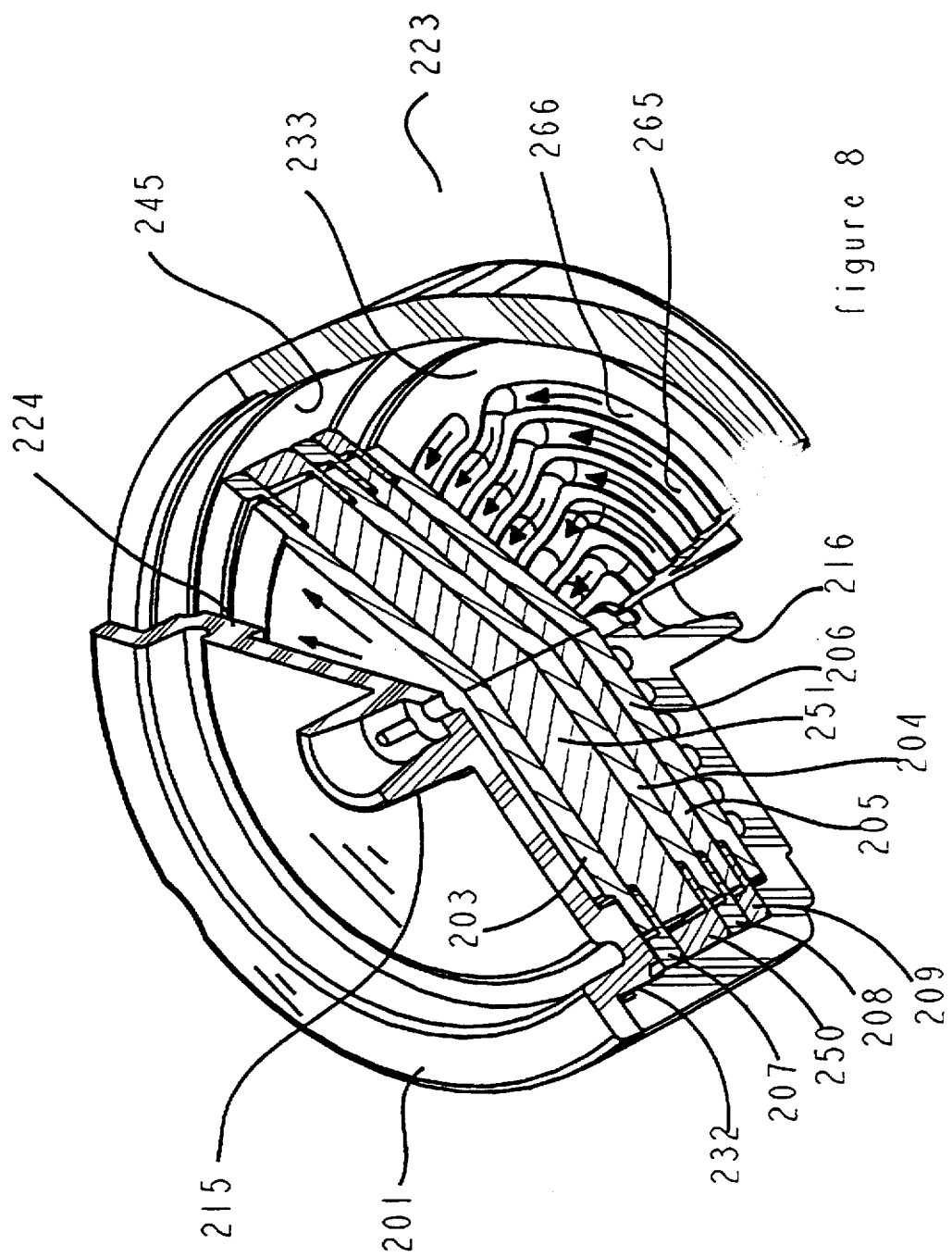
FIG. 8 depicts an isometric view of a filtration device having portions removed therefrom with a spiral channel as a filter support and constructed in accordance with the principles of the present invention.
Figure 9:
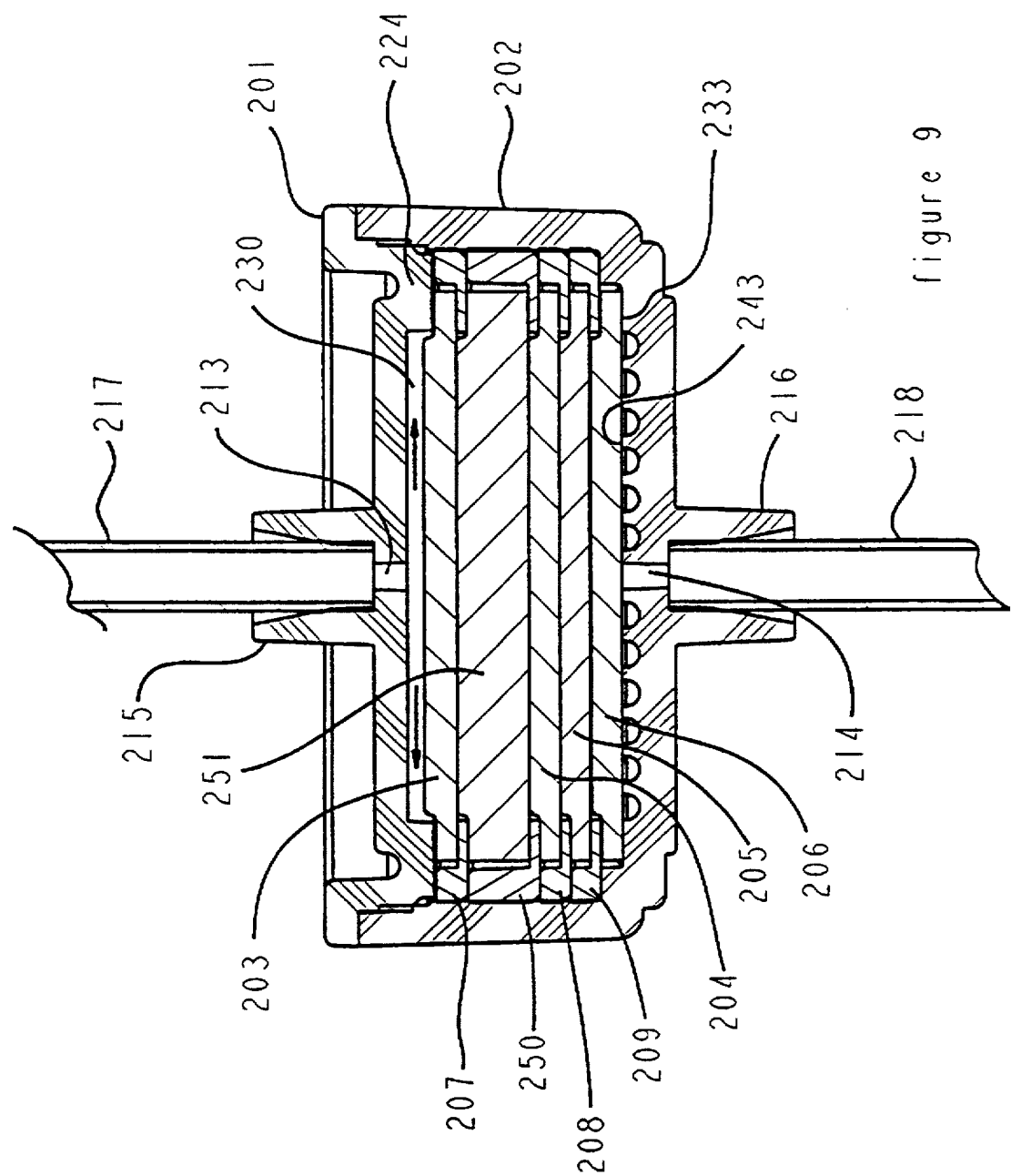
FIG. 9 depicts a sectional representation of the filtration device of FIG. 8 constructed in accordance with the principles of the present invention.
Figure 10:
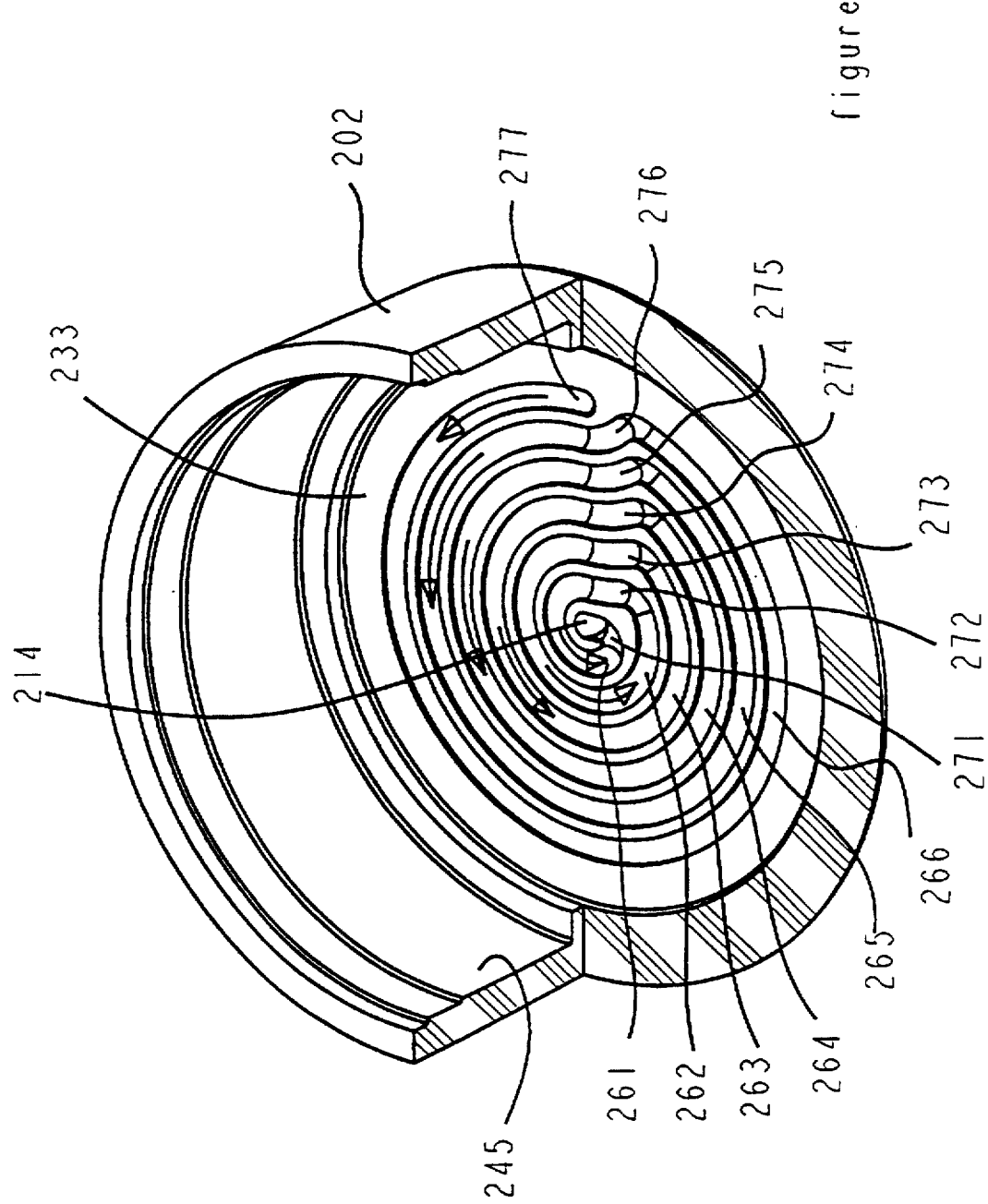
FIG. 10 depicts an isometric view of the outlet section of the filtration device of FIGS. 8 and 9 having portions removed therefrom and constructed in accordance with the principles of the present invention.

A third embodiment of the filtration apparatus constructed in accordance with the principles of the present invention incorporates a modified spiral channel as a filter support and flow deflector as shown in FIGS. 8–10.

Referring to FIGS. 8 and 9, the filtration device 223 includes an inlet section 201 which is sealed to outlet section 202 at a joint 232 therebetween. Preferably, the joint is sealed by an ultrasonic weld, a heat weld, a solvent weld, a glue joint or any other means of creating a leak tight seal. A filter element 206 is sealed into the outlet section 202 by compression thereby forming a seal. The outer periphery of filter element 206 is compressed between shelf 233 located along the interior of the outlet section 202 and seal ring 209. Filter element 205, located on top of filter element 206, is sealed into outlet section 202 using a compression seal. The outer periphery of filter element 205 is compressed between seal ring 208 and seal ring 209. Filter element 204 located on top of filter element 205, is sealed into outlet section 202 also using a compression seal. The outer periphery of filter element 204 is compressed between seal ring 250 and seal ring 208. Filter element 251, located on top of filter element 205, is sealed into outlet section 202 using a compression seal. The outer periphery of filter element 251 is compressed between seal ring 207 and seal ring 250. Filter element 203, located on top of filter element 251, is sealed into outlet section 202 also using a compression seal. The outer periphery of filter element 203 is compressed between seal ring 207 and seal rib 224 protruding in the axial direction along the outer perimeter of inlet section 201. Seal rings 207, 250, 208 and 209 form a press fit with wall 245 of outlet section 202. However, seal rings 207, 250, 208 and 209 may be ultrasonically welded, heat welded, solvent welded, glued or bonded to outlet section 202 using any other means for creating a leak tight seal. If the seal rings are not press fitted into outlet section 202, then seal ring 209 could be bonded to outlet section 202 and the bottom surface of seal ring 208 could be bonded to the top surface of seal ring 209. Likewise the bottom surface of seal ring 250 could be bonded to the top surface of seal ring 208 and the bottom surface of seal ring 207 could be bonded to the top surface of seal ring 250.

Although the filtration device such as that shown illustrated in FIGS. 8 and 9, may contain a plurality of filter elements, not all the filter elements need be identical. For example, in certain blood filtration applications, filter elements 203, 204, 205 and 206 could be used to remove leukocytes, while filter element 251 could be used to remove methylene blue. Moreover, although the filtration device 223 contains 5 filter elements, any number of filter elements may be used therein.

Referring to FIGS. 8 and 10, the modified spiral channel located on the interior surface of the outlet section 202 and facing the filter elements is formed of concentric circular channels 261, 262, 263, 264, 265 and 266. Concentric circular channel 266 communicates, i.e., is in fluid flow relationship, with concentric circular channel 265 via blend channel 276. Concentric circular channel 265 communicates with concentric circular channel 264 via blend channel 275. Concentric circular channel 264 communicates with concentric circular channel 263 via blend channel 274. Concentric circular channel 263 communicates with concentric circular channel 262 via blend channel 273. Concentric circular channel 262 communicates with concentric circular channel 261 via blend channel 272. Concentric circular channel 261 communicates with outlet port 214 via blend channel 271.

Preferably, both the concentric circular channels and the blend channels have a round bottom (FIG. 9). However, these channels may have a square bottom, a V-shaped bottom or a bottom of a other shapes. The concentric circular channels allow for the proper draining of filtrate in order to maximize the entire surface area of a circular filter element for filtration.

When filter element 206 is sealed in place in outlet section 202, the bottom surface 243 of filter element 206 overlays the open top of the concentric circular channels and blend channels. Therefore, the continuous channel formed by the concentric circular channels interconnected by the blend channels overlayed by bottom surface 243 of filter element 206 acts as a length of tube wrapped in the shape of the modified spiral channel with one face (i.e. the bottom surface 243 of filter element 206) being porous to allow filtrate to enter therein. Although the filtration device of FIGS. 8 and 9, uses six concentric circular channels to form the modified spiral channel, a different number of concentric circular channels may be used. Although the device illustrated uses a continuous modified spiral channel, the channel could be a continuous channel of any shape. Multiple continuous channels could also be used. For example, a pair of parallel modified spiral channels could also be used.

The filtration device 223 is placed in an operational assembly and used in the same manner as the embodiment depicted in FIGS. 1 and 2, and as shown in FIG. 4. During filtration, the filtration device 223 hangs in line. Liquid enters the filtration device 223 from its inlet port 213 and liquid exits the filtration device 223 from its outlet port 214. In the process of filling the filtration device 223 with liquid, such as blood for filtration, all of the air that was in the filtration apparatus 223 before the filtration process began is purged out of the filtration apparatus 223, through outlet tube 218 into a receiving blood bag (not shown). Therefore, little or no air is trapped in the filter elements 203, 251, 204, 205, 206 and the entire exposed surface area of the filter elements is used for filtration.

Referring to FIGS. 8 and 9, fluid such as bloods flows from, for example, feed blood bag (not shown) through inlet tube 217, through inlet port 213, into upper chamber 230. The air that was in inlet tube 217 will be forced down stream ahead of the blood flow into upper chamber 230. Blood enters upper chamber 230 in the center of upper chamber 230. Therefore, upper chamber 230 will fill from the center radially outward. This radial flow is illustrated by arrows in FIGS. 8 and 9. As upper chamber 230 fills from its center radially outward the air in upper chamber 230 will be forced through the non wet portions of filter elements 203, 251, 204, 205 and 206 into a modified spiral channel, through outlet port 214, through outlet tube 218, into the receiving blood bag (not shown).

Because upper chamber 230 fills from the center radially outward filter elements 203, 251, 204, 205 and 206 will wet from the center radially outward. It is desirable to make the height of upper chamber 230 small enough in relation to the initial blood flow rate to assure that all of the air initially in upper chamber 230 will be forced through filter elements 203, 251, 204, 205 and 206. However, if a pocket of air is left above the blood level in upper chamber 230 the device will still function properly. As the filter elements wet radially outward the air that was in the filter elements will be forced into the modified spiral channel, through the outlet port 214, through outlet tube 218, into receiving blood bag (not shown). Because the filter elements wet from the center radially outward, blood will first flow out of filter element 206, into the modified spiral channel from its center and then continue to flow out of filter element 206 in a radially outward pattern. This causes blood to flow out of outlet port 214 before all of the air is purged from filter elements 203, 251, 204, 205 and 206. Therefore, some air initially is trapped in the modified spiral channel. However, since the outside of receiving blood bag (not shown) is at atmospheric pressure, as blood starts to fill outlet port 214 and outlet tube 218 a negative head pressure develops at the outlet port 214 end of the modified spiral channel. This negative pressure sucks the trapped air out of the modified spiral channel. Therefore, once blood starts to fill outlet tube 218 a stream of blood and air segments will flow through outlet tube 218 into receiving blood bag (not shown) until all of the air is purged from filter elements 203, 251, 204, 205 and 206 and from the modified spiral channel. Once all air is purged, only liquid will flow from outlet tube 218 into the receiving blood bag (not shown).

Figure 11:
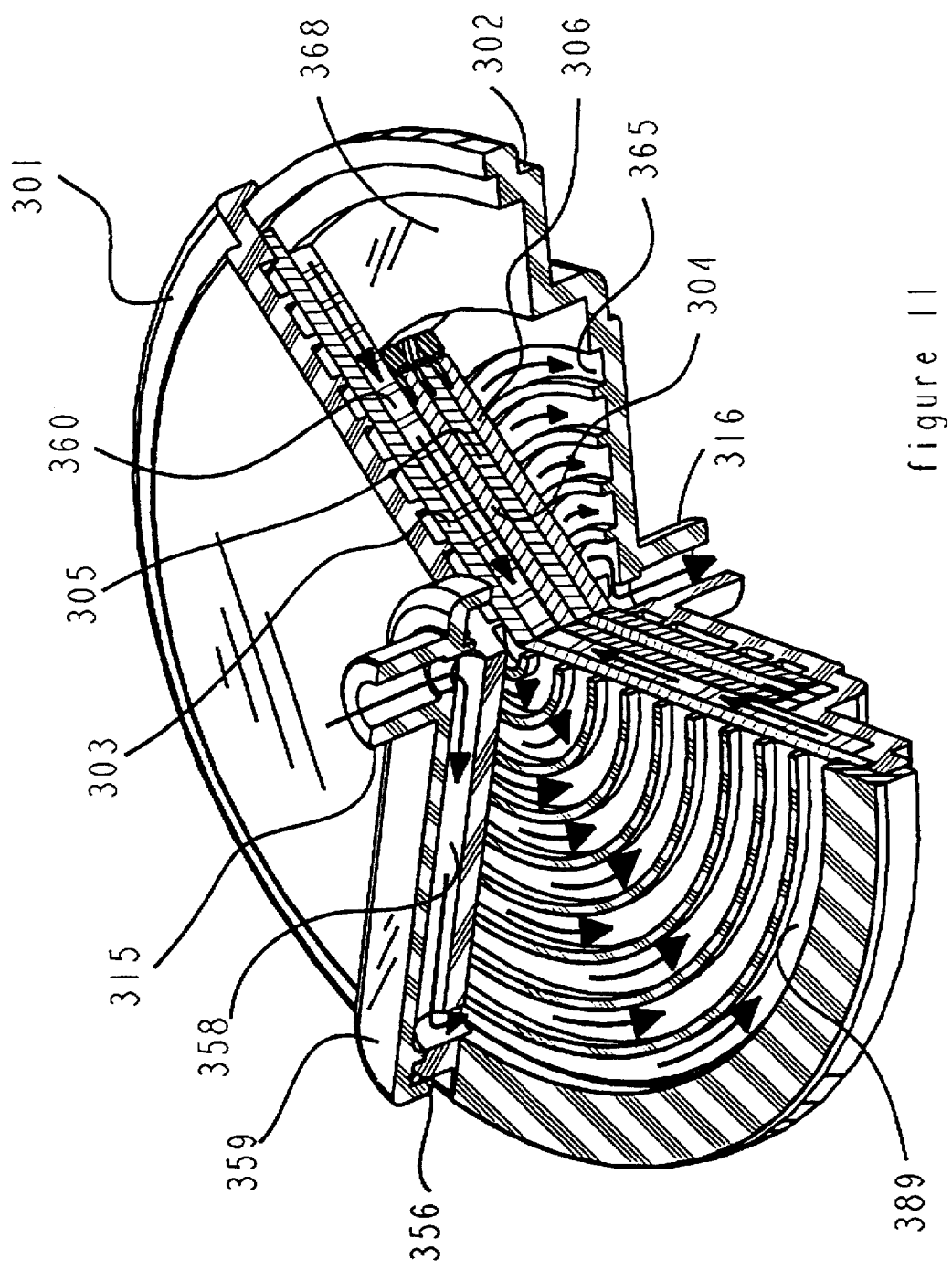
FIG. 11 depicts an isometric view of another embodiment of the filtration device having a first and second modified spiral channel having portions removed therefrom and usable in accordance with the principles of the present invention.
Figure 12:
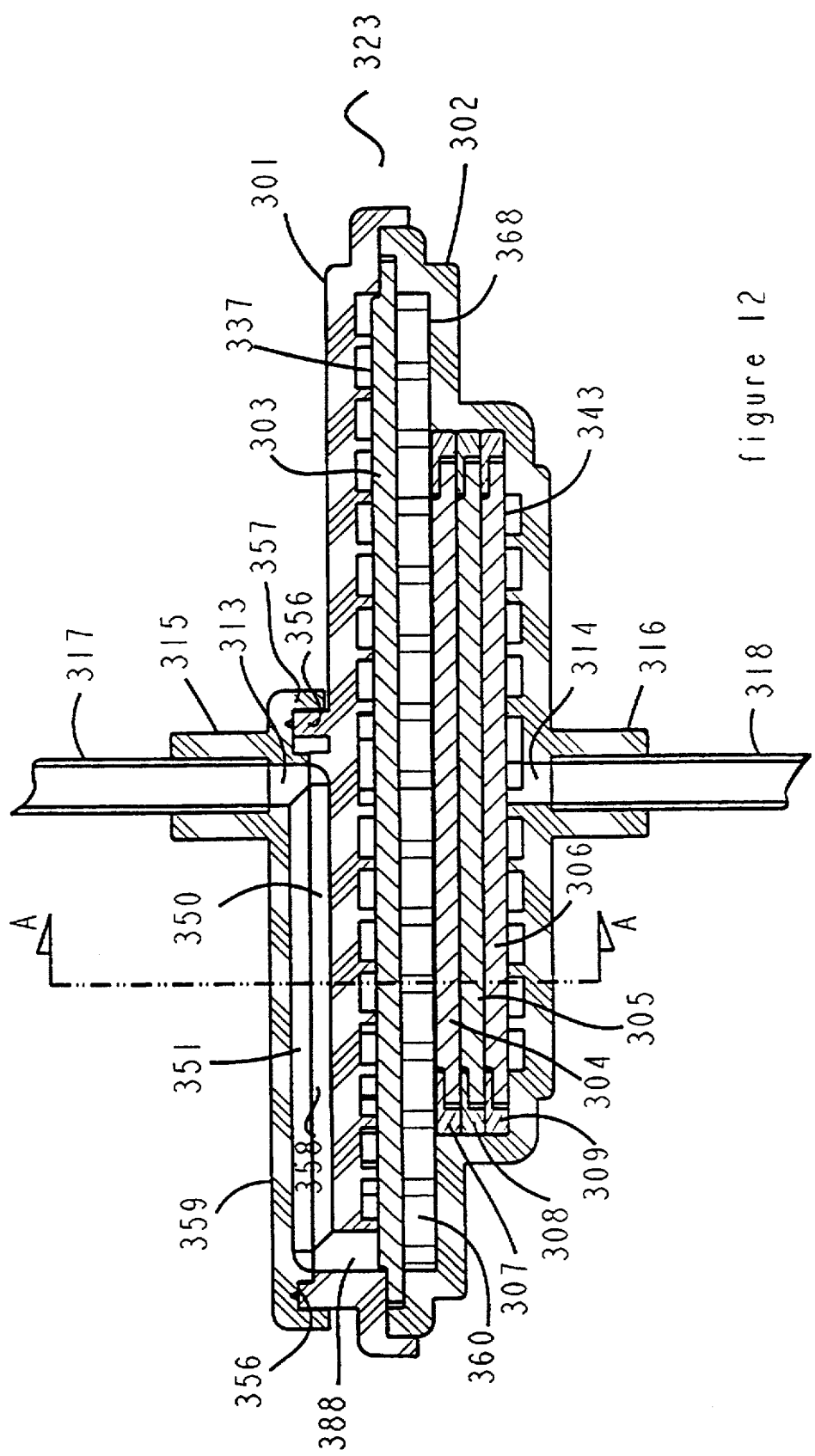
FIG. 12 depicts a sectional representation of the embodiment of the filtration device of FIG. 11 constructed and usable in accordance with the principles of the present invention.

A fourth embodiment of the filtration apparatus constructed in accordance with the principles of the present invention uses both a first modified spiral channel as a filter support and downstream flow director, and a second modified spiral channel as an upstream flow director as shown in FIGS. 11 and 12. This filtration device also incorporates a midstream screen.

Figure 15:
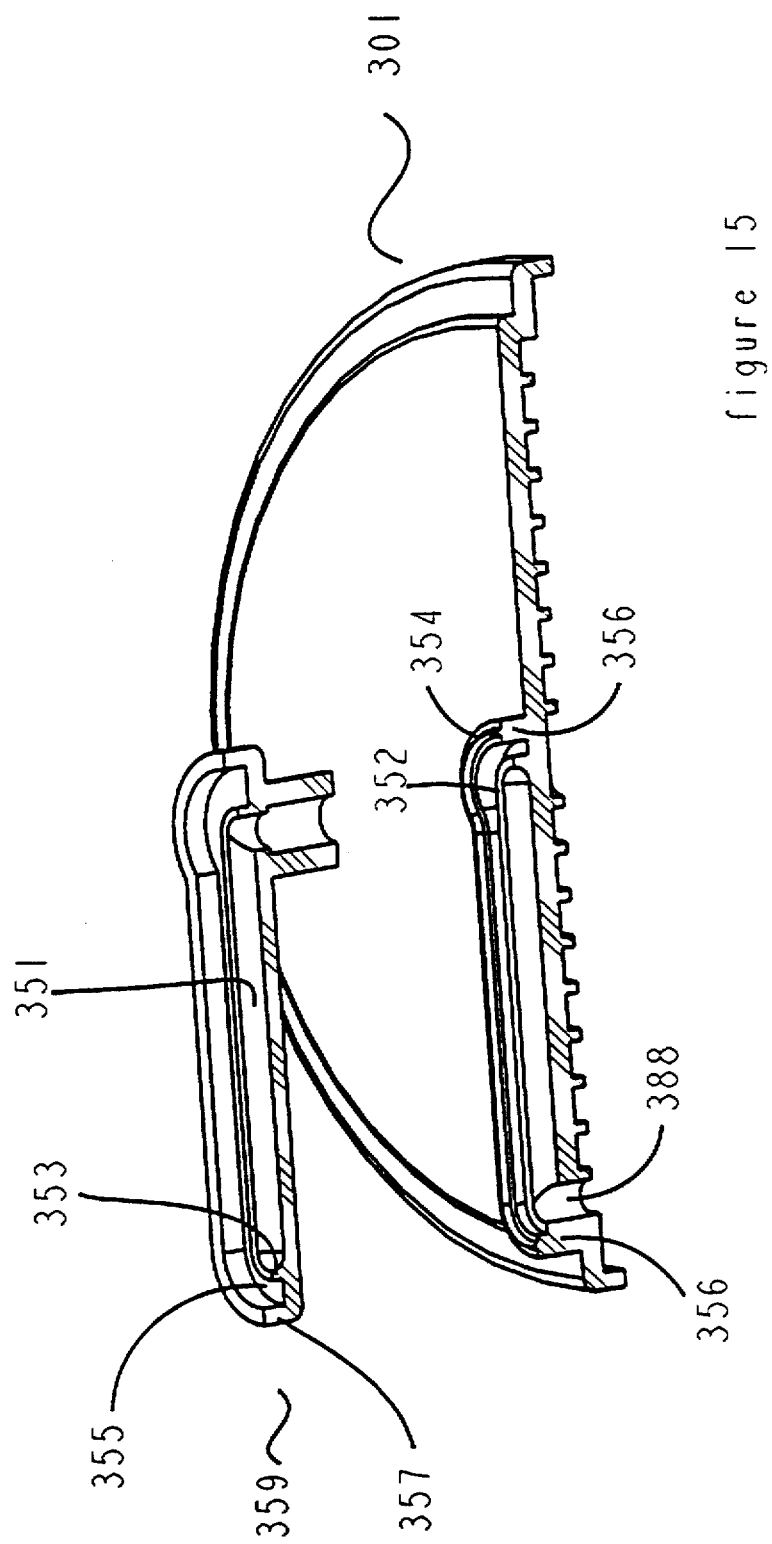
FIG. 15 depicts an exploded isometric view having portions removed therefrom of the inlet section and the inlet cover of the filtration device depicted in FIGS. 11 and 12 and constructed in accordance with the principles of the present invention.
Figure 16:
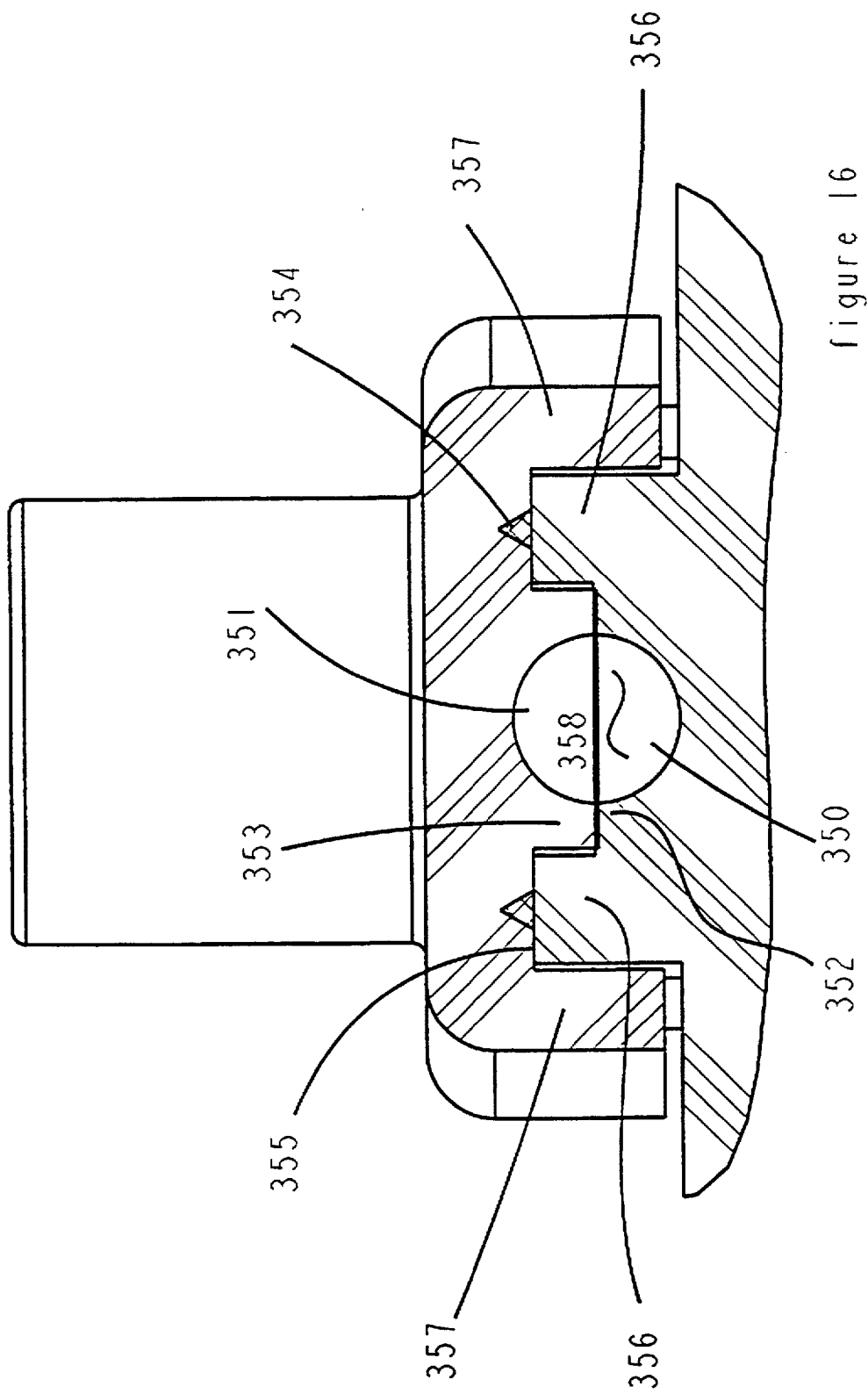
FIG. 16 depicts a cross-sectional view of the inlet cover disposed upon the inlet half of the filtration device depicted in FIGS. 11 and 12 and constructed in accordance with the principles of the present invention.

Referring to FIGS. 11, 15 and 16, an inlet cover 359 is bonded to the outer surface of the inlet section 301 to form flow diverter channel 358. A rib 356 of inlet section 301 contains energy director 354 and supports the inlet cover 359. Skirt 357 defines the outer periphery of the inlet cover 359 and acts as both an alignment means to align inlet cover 359 with rib 356 of inlet section 301 and as a flash trap to prevent any over weld, which could cause cuts on the hands of operators, from being exposed on the outside of the device. An ultrasonic weld of the inlet cover 359 is made by energy director 354, thus sealing the top surface of rib 356 of inlet section 301 to surface 355 of inlet cover 359. The weld is complete when rib 353 of inlet cover 359 is pressed against rib 352 of inlet section 301. Once the weld is complete and rib 353 of inlet cover 359 is in contact with rib 352 of inlet section 301 the half round channel 351 of inlet cover 359 combined with the half round channel 350 of inlet section 301, form round radial diversion channel 358 which diverts liquid flow radially outward from inlet port 313 to concentric circular channel 389 of inlet section 301. This joint design results in round diversion channel 358 without sharp edges which could rupture cells in blood being filtered.

Figure 13:
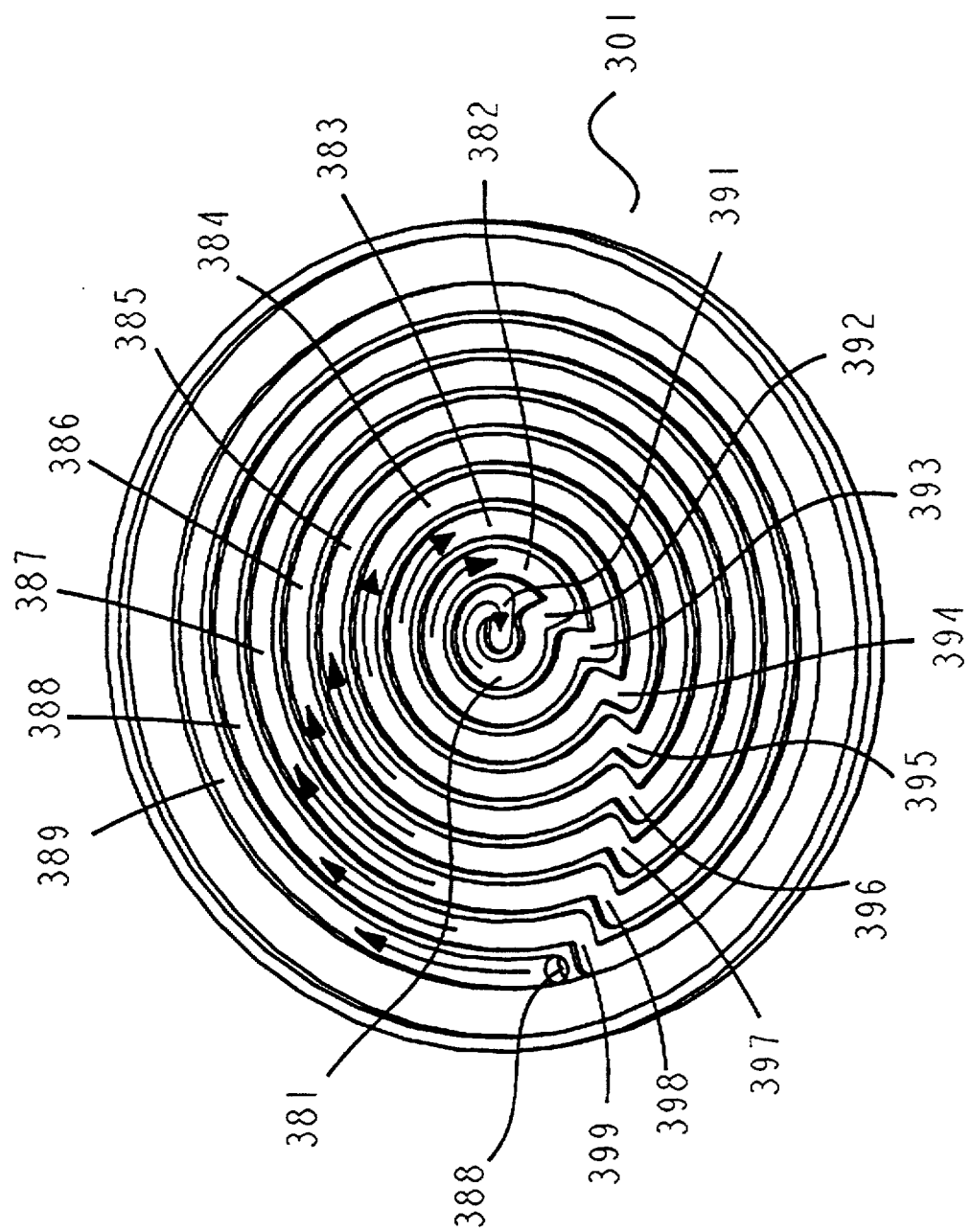
FIG. 13 depicts an isometric view of the modified spiral channel located on the inside of the inlet section of the filtration device depicted in FIGS. 11 and 12, constructed in accordance with the principles of the present invention.

Referring to FIGS. 11 and 13, the inlet section 301 contains upper modified spiral channel comprised of concentric circular channels 381, 382, 383, 384, 385, 386, 387, 388 and 389. As shown in FIG. 15, concentric circular channel 389 communicates, i.e., is in fluid flow relationship, with concentric circular channel 388 via radial channel 399. Concentric circular channel 388 communicates with concentric circular channel 387 via radial channel 398. Concentric circular channel 387 communicates with concentric circular channel 386 via radial channel 397. Concentric circular channel 386 communicates with concentric circular channel 385 via radial channel 396. Concentric circular channel 385 communicates with concentric circular channel 384 via radial channel 395. Concentric circular channel 384 communicates with concentric circular channel 383 via radial channel 394. Concentric circular channel 383 communicates with concentric circular channel 382 via radial channel 393. Concentric circular channel 382 communicates with concentric circular channel 381 via radial channel 392. Concentric circular channel 381 communicates with the center of inlet half 301 via radial channel 391.

As shown in FIGS. 11 and 12, the concentric circular channels and the radial channels have a square cross-section. These channels could however, have a round cross-section, a V-shaped cross-section, or other shape. Using this series of connected concentric circular channels provides the proper underdrain to utilize the entire exposed surface area of a circular filter element. The concentric circular channels together with the radial channels form a continuous channel starting at the port 388 of concentric circular channel 389 and ending at center of inlet section 301. Radial diversion channel 358 communicates with concentric circular channel 389 via port 388. When filter element 303 is sealed in place its top surface 337 underlays the open bottom of the concentric circular channels and of the radial channels of inlet section 301. Therefore, the continuous channel formed by the concentric circular channels interconnected by the radial channels of inlet section 301 and underlayed by top surface 337 of filter element 301 essentially forms a length of tube in the shape of the modified spiral channel with one face (i.e. the top surface 337 of filter element 301) being porous. Although the filtration device 323 uses nine concentric circular channels to form the upper modified spiral channel on the inlet section 301 any number of concentric circular channels could be used.

Figure 14:
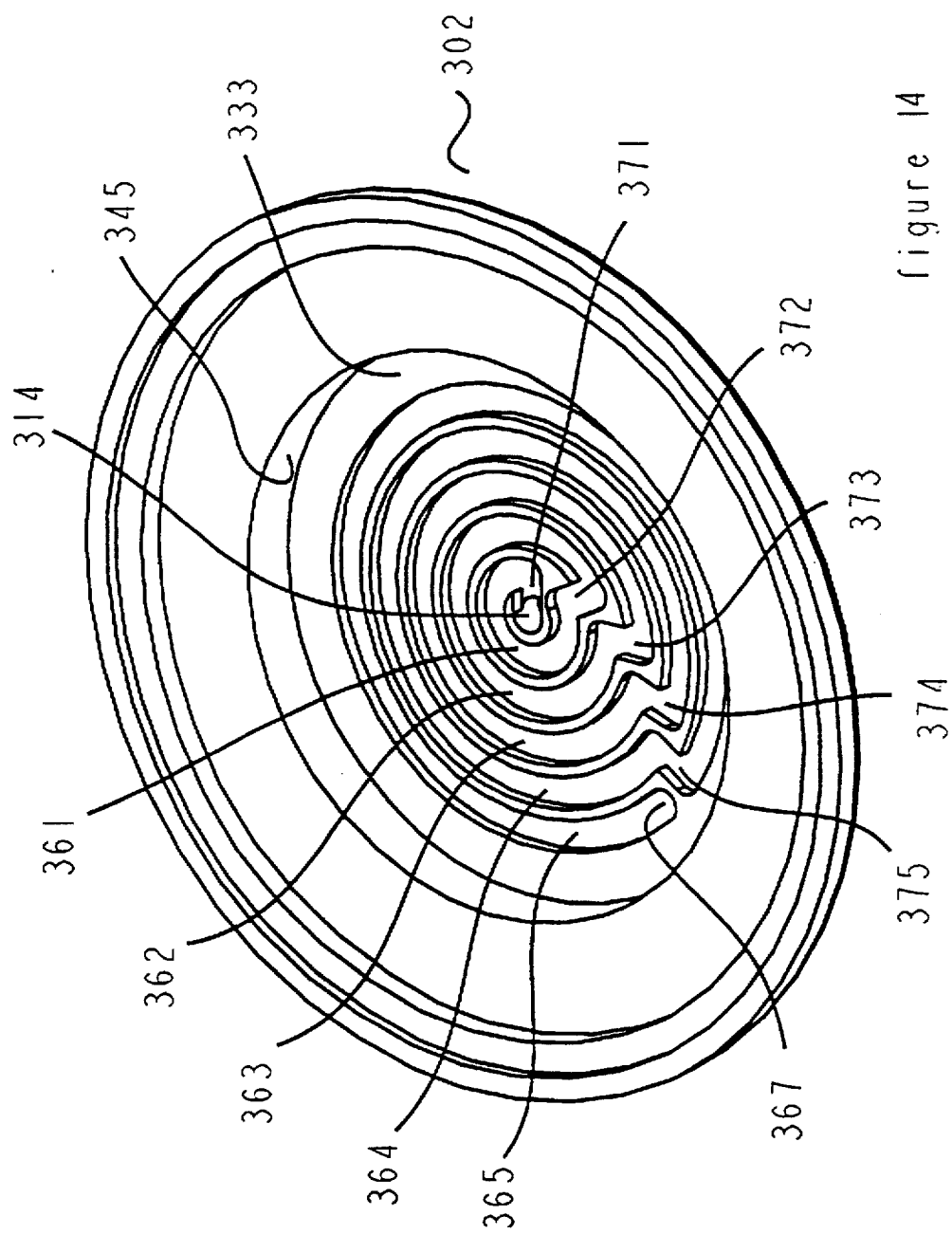
FIG. 14 depicts an isometric view of the modified spiral channel located on the inside of the outlet section of the filtration device depicted in FIGS. 11 and 12 and constructed in accordance with the principles of the present invention.

Referring to FIGS. 11 and 14, a modified spiral channel located on the outlet section 302 includes concentric circular channels 361, 362, 363, 364, and 365. Concentric circular channel 365 communicates with concentric circular channel 364 via radial channel 375. Concentric circular channel 364 communicates with concentric circular channel 363 via radial channel 374. Concentric circular channel 363 communicates with concentric circular channel 362 via radial channel 373. Concentric circular channel 362 communicates with concentric circular channel 361 via radial channel 372. Concentric circular channel 361 communicates with outlet port 314 via radial channel 371.

As shown in FIG. 12, the concentric circular channels and the radial channels of the lower modified spiral channel have a square bottom. These channels could however, have a round bottom, a V-shaped bottom or other shape. Using this series of connected concentric circular channels allows for the proper underdrain so that the entire exposed surface area of a circular filter element is used for filtration. Referring to FIG. 14, the concentric circular channels together with the radial channels form a continuous channel starting at the beginning 367 of concentric circular channel 365 and ending at outlet port 314 of outlet section 301. When filter element 306 is sealed in place between inlet section 301 and outlet section 302, the bottom surface 343 of filter element 306 provides a surface which overlays the top of the concentric circular channels and of the radial channels of outlet section 302. Therefore, the continuous channel formed by the concentric circular channels interconnected by the radial channels of outlet section 302 and overlayed by bottom surface 343 of filter element 306 essentially forms a length of tube wrapped in the shape of the modified spiral channel with one face (i.e. the bottom surface 343 of filter element 306) being porous. The filtration device 323 shown in FIGS. 11 and 12, uses five concentric circular channels to form the lower modified spiral channel of outlet section 302. However, any number of concentric circular channels could be used. Although outlet section 302 uses a continuous modified spiral channel, the channel could be a continuous channel of any shape. Multiple continuous channels could also be used. For example a pair of parallel modified spiral channels could also be used.

Referring to FIGS. 11 and 12, the means for supporting the filter element 303 includes the midstream screen 360 which sits into well 368 between filter element 304 and filter element 303. Midstream screen 360 may be composed of any means that will support filter element 303 while allowing for radial flow therein. Examples of materials that can be used for midstream screen 360 are woven and non woven screen material columns, blocks, etc. Midstream screen 360 could also be made as a molded part. Filter elements 304, 305, 306 are sealed in place by sealing rings 307, 308, 309 as well as outlet section 302, in the same manner as previously disclosed for filtration devices 23, 123, discussed supra.

The filtration device 323 is used in the same manner as previously discussed in reference to the embodiments of the filtration device 23 shown in FIGS. 1 and 2, and is placed in operational assembly in the same manner as depicted in FIG. 4. Referring to FIGS. 11 and 12, fluid such as blood may flow from a feed blood bag (not shown) through inlet tube 317, through inlet port 313, into diverter channel 358. Diverter channel 358 diverts the blood flow radially outward to port 388. From port 388, the blood flows into the modified spiral channel of inlet section 301. The blood flow then flows through the modified spiral channel of inlet section 301 starting from concentric circular channel 389 and ending in the center of inlet section 301. As the flow progresses from outermost concentric circular channel 389 to the center of inlet section 301 filter element 303 will wet from its outer periphery radially inward to its center. Therefore, blood will start to flow out of filter element 303 into midstream screen 360 from the outer periphery of filter element 303 and continue to flow out of filter element 303 into midstream screen 360 in a radially inward pattern. This radial inward filling of midstream screen 360 forces the air that is being purged from filter element 303 as it wets and the air in midstream screen 360 through filter elements 304, 305, 306, through the modified spiral channel of outlet section 302, through outlet tube 318 and into the receiving blood bag.

Because midstream screen 360 fills from its outer periphery radially inward, filter elements 304, 305 and 306 will wet from their outer periphery radially inward. Hence the modified spiral channel of outlet section 302 will fill from its outermost concentric circular channel 365 radially inward to outlet port 314. Depending on the alignment of the modified spiral channel of inlet section 301 in relation to the alignment of the modified spiral channel of outlet section 302, some air may be initially trapped in the modified spiral channel of outlet section 302 as modified spiral channel of outlet section 302 fills with blood. Since the outside of the receiving blood bag (not shown) is at atmospheric pressure as blood starts to fill outlet port 314 and outlet tube 318, a negative head pressure develops at the outlet port end of the lower modified spiral channel of outlet section 302. This negative pressure creates a suction that will force any trapped air out of the lower modified spiral channel of outlet section 302.

Referring to FIGS. 11 and 12, the diameter of filter element 303 is greater than the diameter of filter elements 304, 305 and 306. Also, the diameter of midstream screen 360 is equal to the usable diameter of filter element 303. Once filtration device 323 has been wet with blood, (i.e. all of the air has been purged from filtration device 323) the blood that flows out of filter element 303 from the region of filter element 303 that is beyond the exposed area of filter elements 304, 305 and 306, will flow radially inward through midstream screen 360 to the exposed area of filter elements 304, 305 and 306. Hence, even though filter element 303 is of greater surface area than filter elements 304, 305, 306, all of the surface area of all of the filter elements 303, 304, 305, 306 will be utilized for filtration.

Midstream screen 360 provides a means to fully utilize the surface area of one or more filter elements, that have a greater exposed surface area than downstream filter elements for filtration. Although the filtration device 323 uses four filter elements, any number of filter elements may be used. Moreover, when using filtration device 323 to remove leukocytes from blood the first filter element 303 usually effectively removes most of the leukocytes. Therefore, it is not necessary to have as much surface area in subsequent downstream filter elements. Also, by reducing the surface area of filter elements 304, 305, 306, the volume of blood left within the filtration device 323 is minimized. Therefore, more filtered blood will be recovered in a receiving blood bag.

Figure 17:
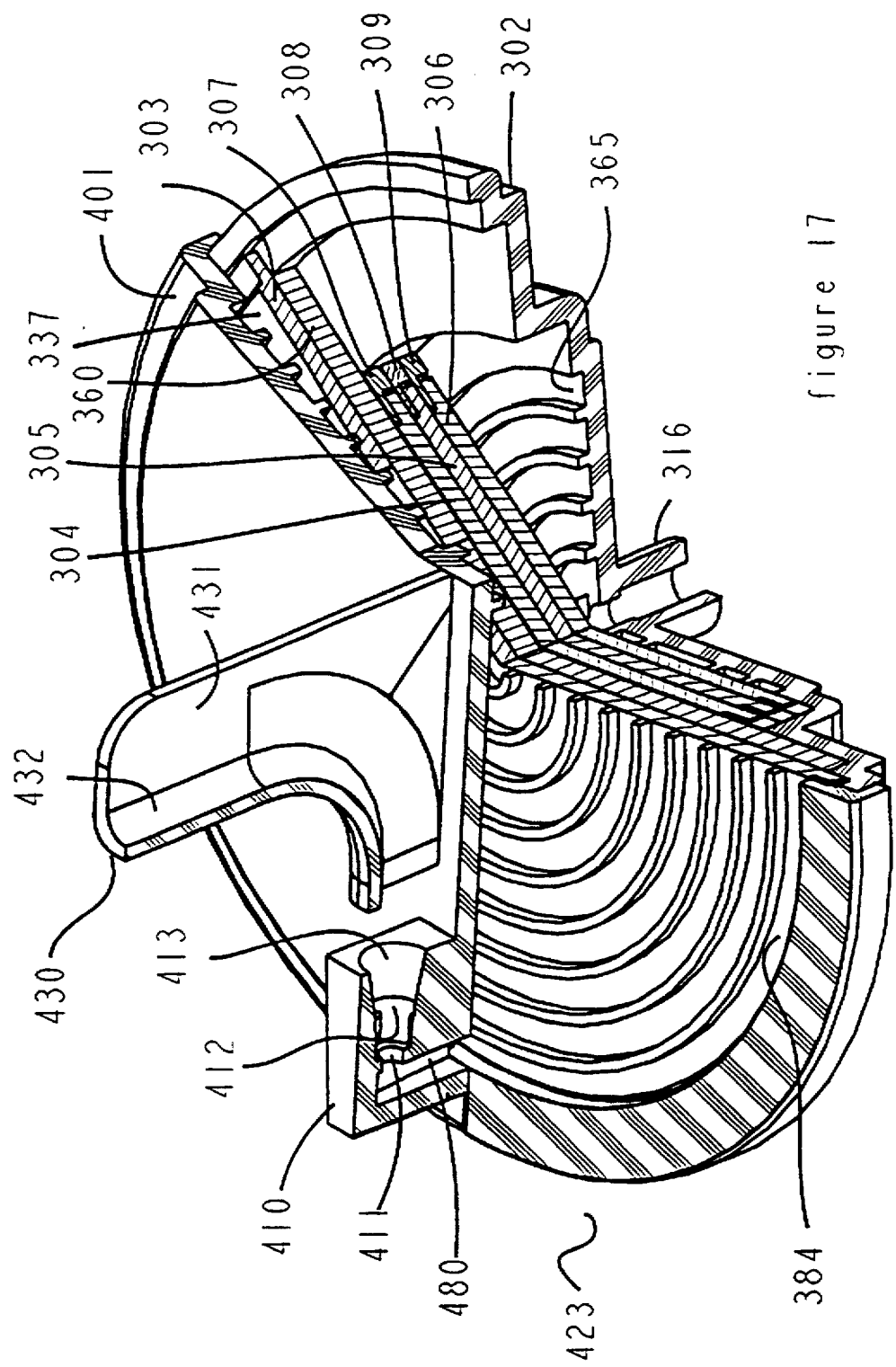
FIG. 17 depicts a sectional isometric view having portions removed therefrom of the filtration device with a modified spiral channel as a filter support and a tube guide useable in accordance with the principles of the present invention.
Figure 18:
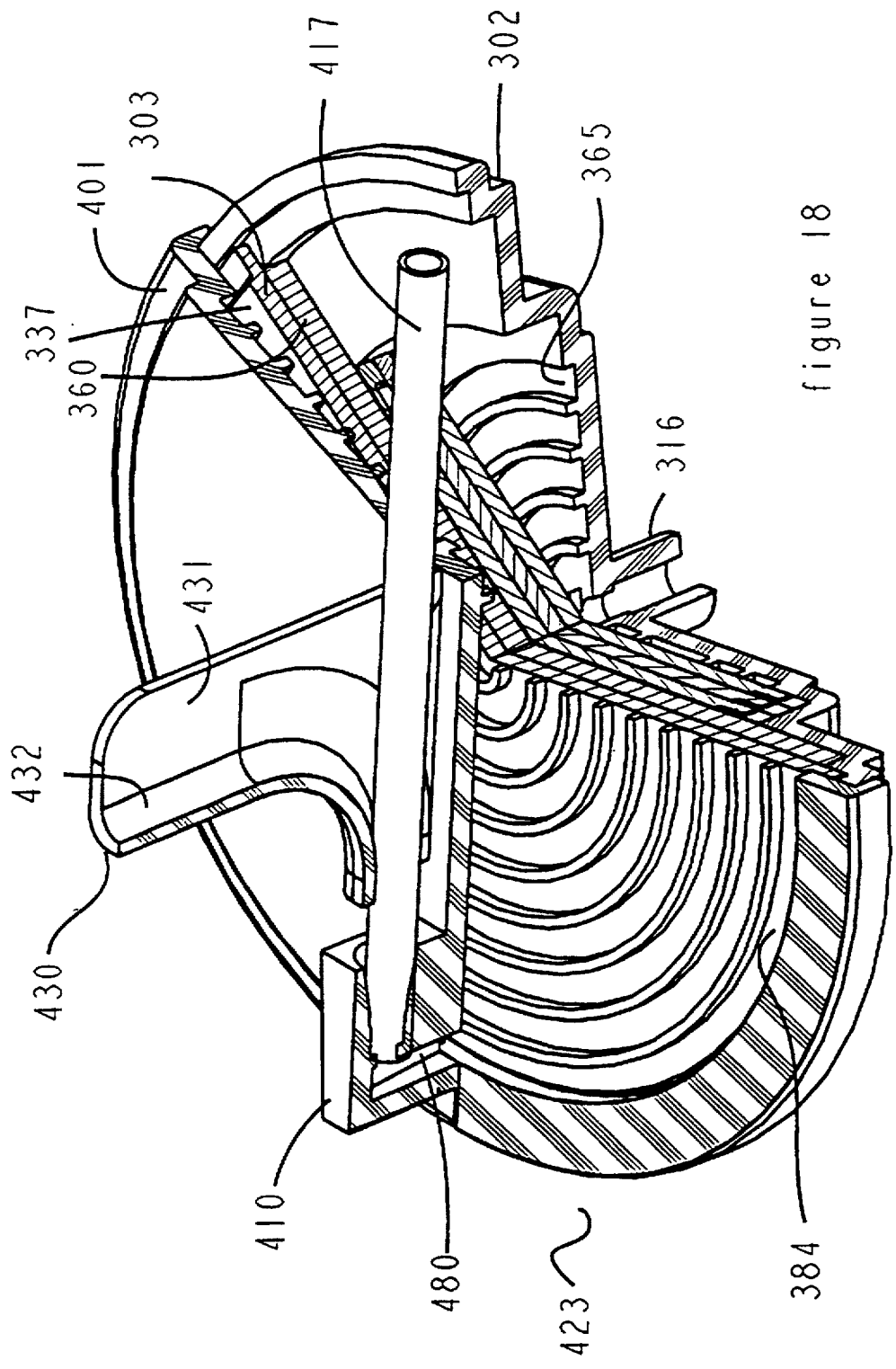
FIG. 18 depicts a sectional isometric view having portions removed therefrom of the filtration device depicted in FIG. 17 having a length of tubing connected thereto.
Figure 19:
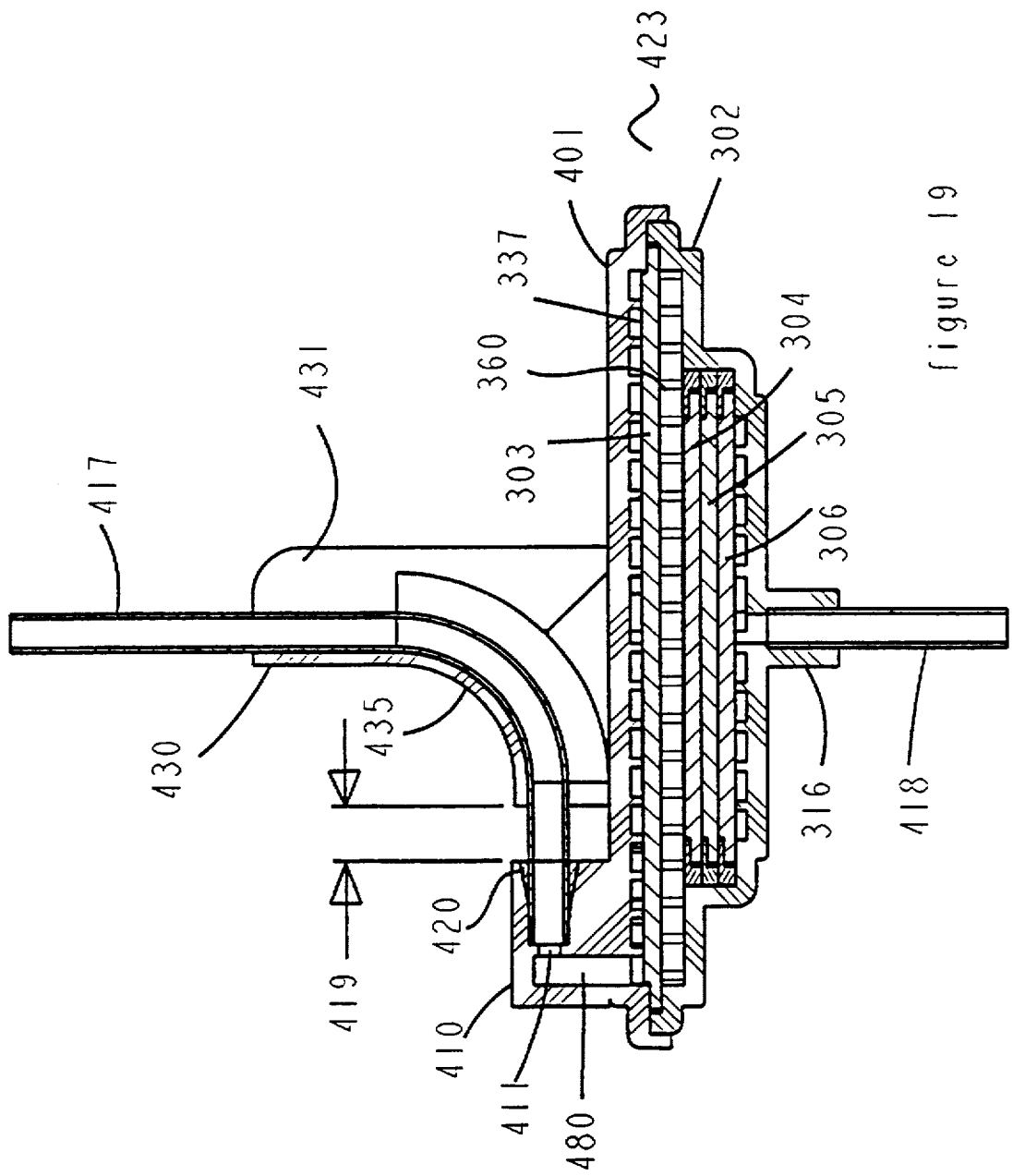
FIG. 19 depicts a sectional representation of the filtration device of FIG. 17 with a length of tubing bent in conformance with the tube guide.

A fifth embodiment of the filtration apparatus constructed in accordance with the principles of the present invention is illustrated in FIGS. 17, 18 and 19. This device is similar to the embodiment of the filter device depicted in FIGS. 11 and 12. However, device 423 of FIGS. 17, 18 and 19, utilizes a different inlet section 401. All of the other parts of filtration device 423 are similar to those in filtration device 323. Therefore, filtration device 423 filters and vents gases such as air similar to filtration device 323. Inlet section 401 of filtration device 423 contains a tube guide 430 and a right angle port assembly 410 which help reduce tube kinking at the interface between the tube and the right angle port assembly 410 as described below.

Most blood filtration devices, including the devices described herein are designed as sterile, disposable blood filtration devices. It is important that these devices be packaged in a manner that will eliminate any kinks in either the inlet or outlet tube of the device. Kinks at the interface where the tube is bonded to the filtration device are common.

Figure 20:
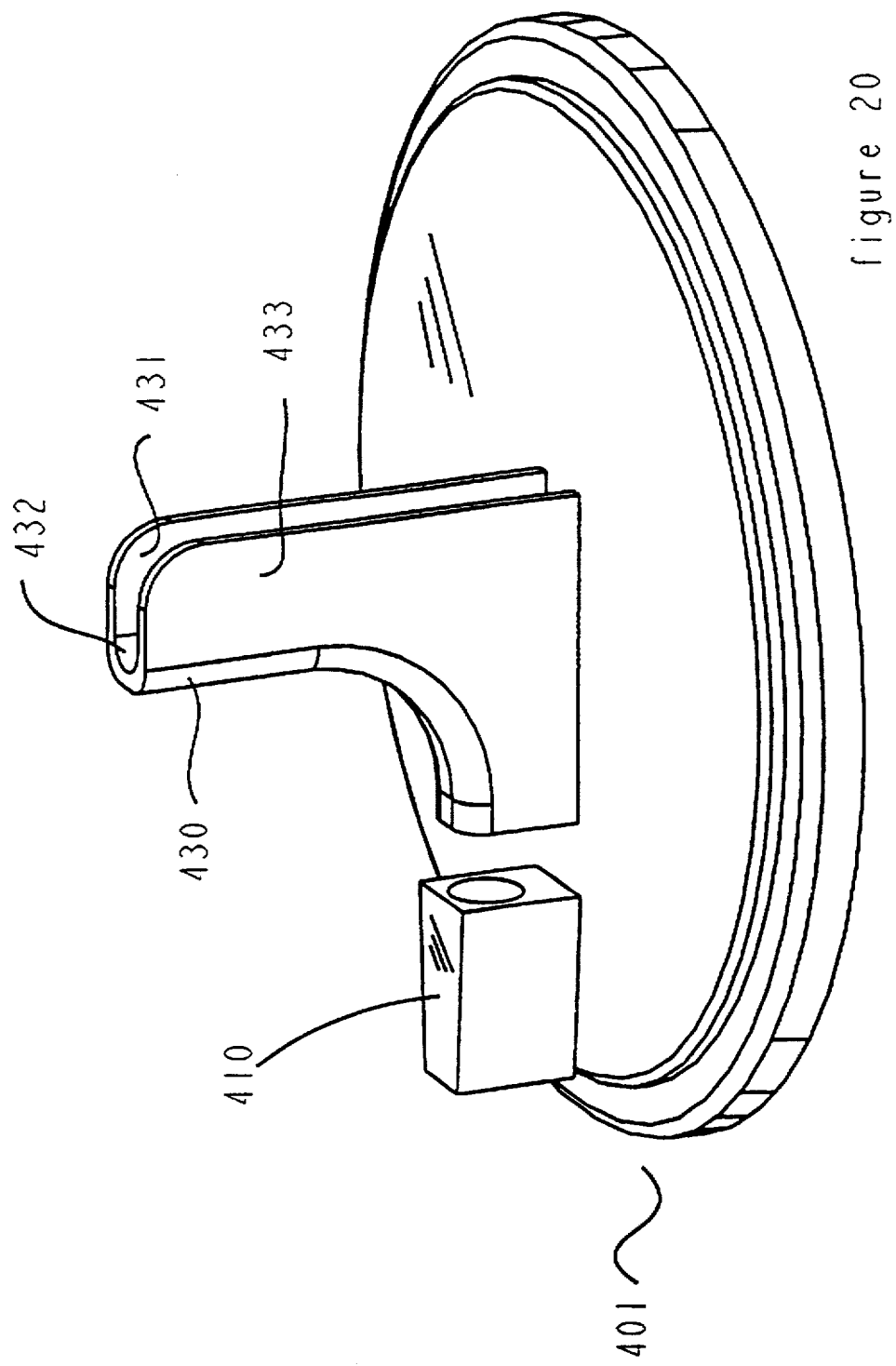
FIG. 20 depicts a top isometric view of the inlet section of the filtration device of FIGS. 17–19 having the tube guide affixed thereto.

Inlet section 401 contains right angle port assembly 410 and tube guide 430. Referring to FIGS. 19 and 20, inlet tube 417 may be bonded to right angle port assembly 410. When packaged and ready for shipment inlet tube 417 may lie straight as illustrated in FIG. 18. However, a longer tube could be coiled and an in-line vent filter could also be provided. An in-line vent filter is disclosed in U.S. patent application Ser. No. 08/209,523, entitled "A Filtration Device Usable for Removal of Leukocytes and Other Blood Components, filed on Mar. 10, 1994, which is hereby incorporated by reference and made a part of the disclosure herein. Tube guide 430 prevents the inlet tube 417 from bending at the interface with right angle port assembly 410 and thereby kinking.

Figure 21:
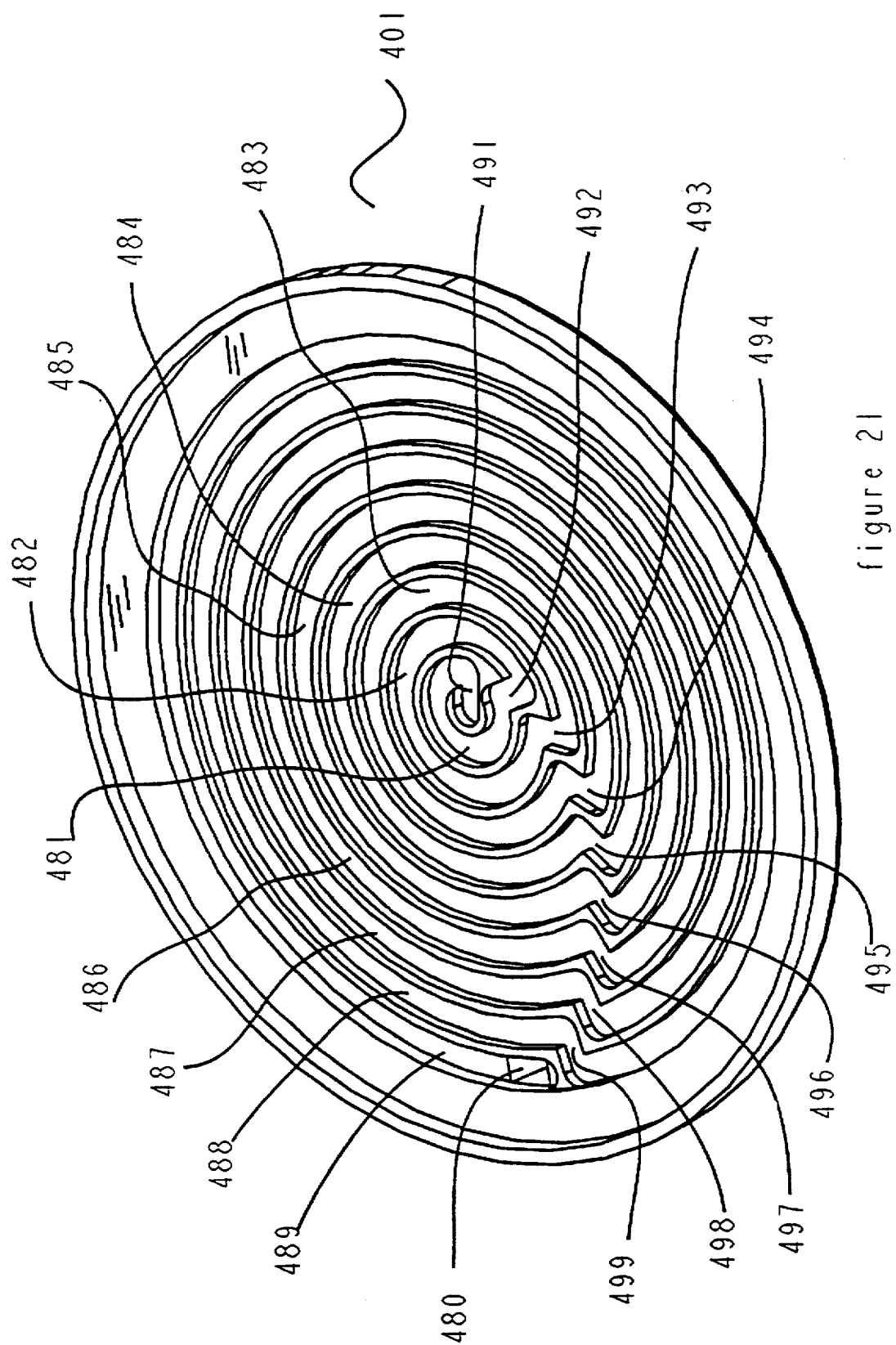
FIG. 21 depicts a bottom isometric view of the inlet section of the filtration device as depicted in FIG. 20 showing the modified spiral channel thereon.

Referring to FIGS. 18 and 21, the inlet section 401 modified spiral channel comprises concentric circular channels 481, 482, 483, 484, 485, 486, 487, 488 and 489. Concentric circular channel 489 communicates with concentric circular channel 488 via radial channel 499. Using this series of connected concentric circular channels provides the proper underdrain to utilize the entire useable surface area of a circular filter element. The concentric circular channels together with the radial channels form a continuous channel starting at the port 480 of concentric circular channel 489 and ending at the center of inlet section 401. When filter element 303 is sealed in place, the top surface 337 of filter element 303 provides a surface to close off the open bottom of the concentric circular channels and of the radial channels of inlet section 401. Therefore, the continuous channel formed by the concentric circular channels interconnected by the radial channels of inlet section 401 and closed off by top surface 337 of filter element 301 essentially forms a length of tube wrapped in the shape of the modified spiral channel with one face (i.e., the top surface 337 of filter element 303) being porous. The device illustrated uses nine concentric circular channels to form the modified spiral channel of inlet section 401. As can be seen from FIG. 21, the modified spiral channel of inlet section 401 is similar to the modified spiral channel of inlet section 303 of the embodiment of the filter device depicted in FIG. 13.

Referring to FIG. 19, the outlet end of inlet tube 417 is bonded to right angle port assembly 410 which is a part of inlet section 401.

Referring to FIG. 19, in use, filtration device 423 is suspended from inlet tube in the same manner as the embodiment of the filtration device 23 shown in FIGS. 1 and 2 and placed in operational assembly in the same manner as depicted in FIG. 4. Inlet tube 417 forms a smooth non-kinked bend around radius 435 of tube guide 430. Thus filtration device 423 hangs plumb from inlet tube 417 even though inlet tube 417 is bonded to right angle port assembly 410 which is located away from the center line of filtration device 423 and at an angle of 90 degrees from the central axis of filtration device 423. Inlet tube 417 communicates with port 480 of right angle port assembly 410 via port 411 of right angle port assembly 410. Hence, blood will flow from inlet tube 417 through port 411 and then through port 480 into outermost concentric circular channel 489. Once the blood enters concentric circular channel 489 of inlet section 401, the filtration device 423 fills, wets and operates the same as filtration device 323 depicted in FIG. 13.

The device as shown in FIG. 19 is oriented so that the center line of the vertical part of inlet tube 417 is aligned with its central axis. In order to allow the filtration device 423 to hang plumb it may be desirable to move the center line of inlet tube 417 away from the central axis of filtration device 423. However, the exact position of the center line of inlet tube 417 may depend on factors such as the weight of the filtration device 423, the stiffness of inlet tube 417, whether or not a right angle tube socket and tube guide are used on outlet section 402, the weight of outlet tube 418 as well as other factors. The combination of right angle the port assembly 410 and tube guide 430 allow inlet tube 417 to lie flat so that inlet tube 417 can be coiled in a non-kinked manner during shipping. Also, the combination of right angle port assembly 410 and tube guide 430 provide a means by which filtration device 423 can hang plumb from inlet tube 417.

Figure 22:
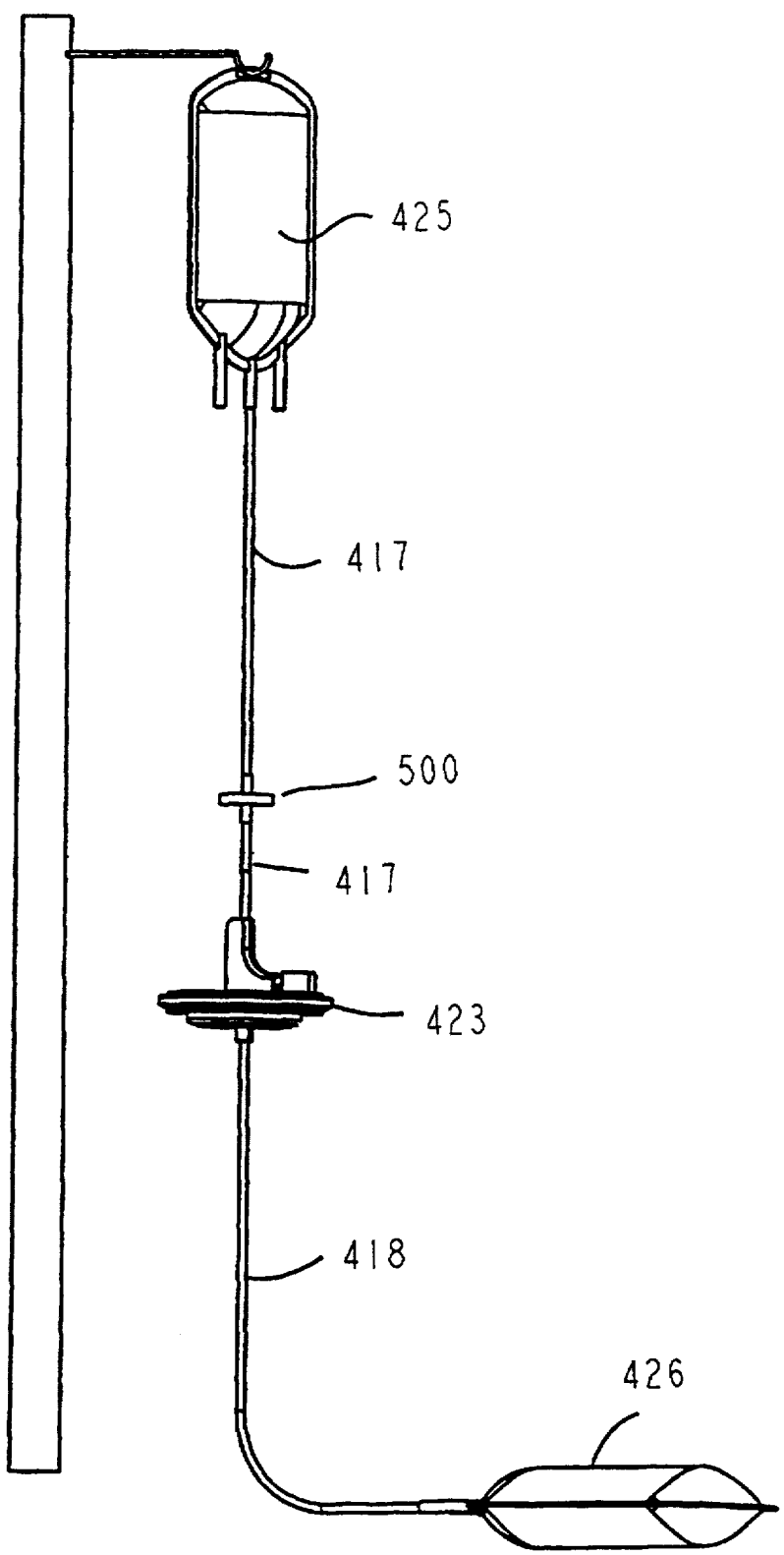
FIG. 22 depicts the filtration device of FIGS. 17–21 in an operational assembly including an in-line vent filter, tubing, blood supply bag and blood collection bag.

Referring to FIG. 22, the filtration device 423 is assembled into a complete blood filtration system. The blood filtration system may also contain inlet tube 417, in-line vent filter 500, feed blood bag 425, outlet tube 418 and receiving blood bag 426. Normally, the system would initially be sterile and feed blood bag 425 would be sterile docked to inlet tube 417 by the end user in a manner well known in the art. When in-line vent filter 500 is used, the blood in inlet tube 417 below in-line vent filter 500 as well as the blood in modified spiral channel of inlet half 401 will be drained into the receiving blood bag 426 at the end of the filtration process. This helps reduce the hold up volume of the system.

Figure 23:
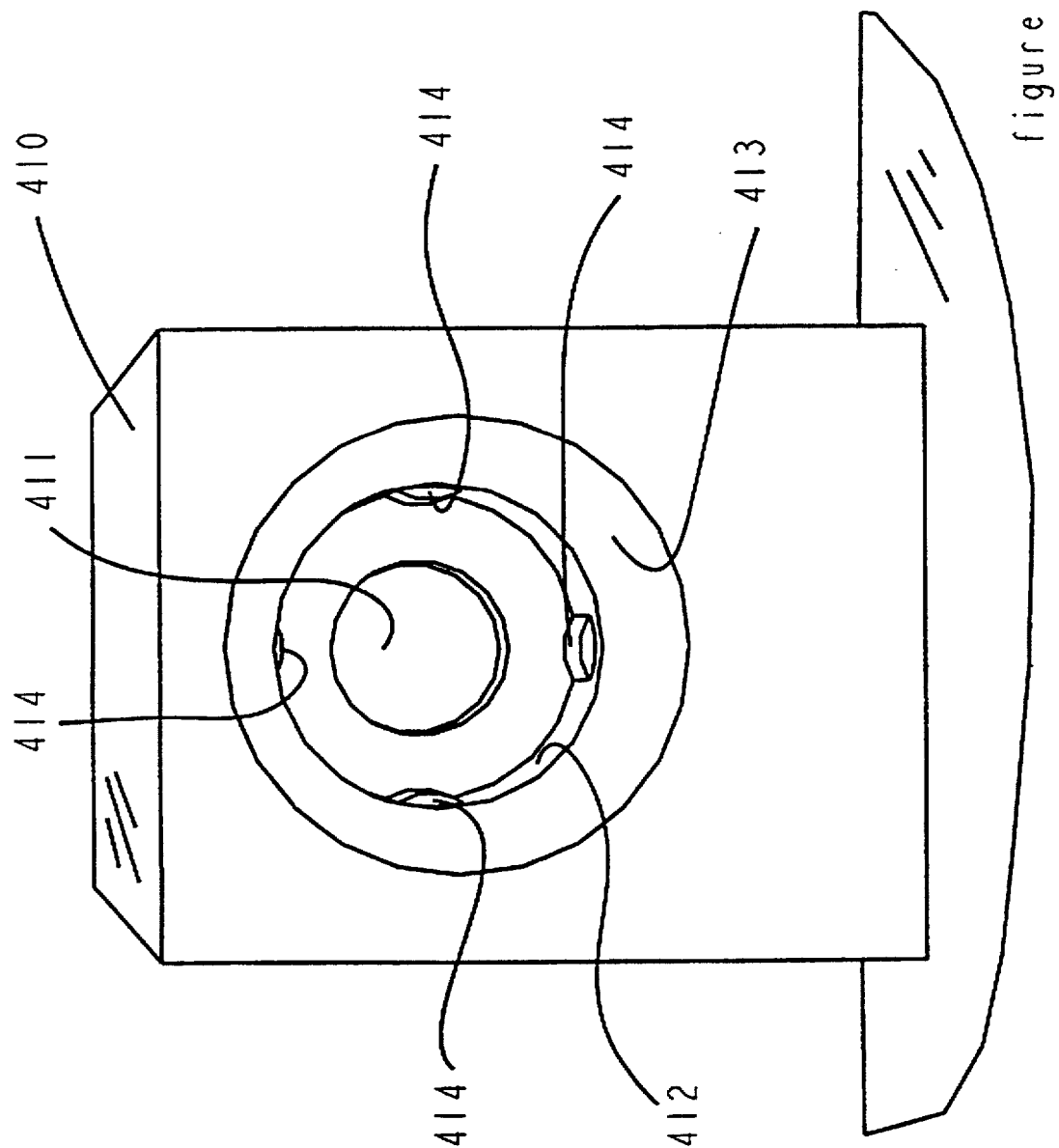
FIG. 23 depicts a front isometric view of a right angle port assembly on the inlet section of the filtration device depicted in FIGS. 17–21.
Figure 24:
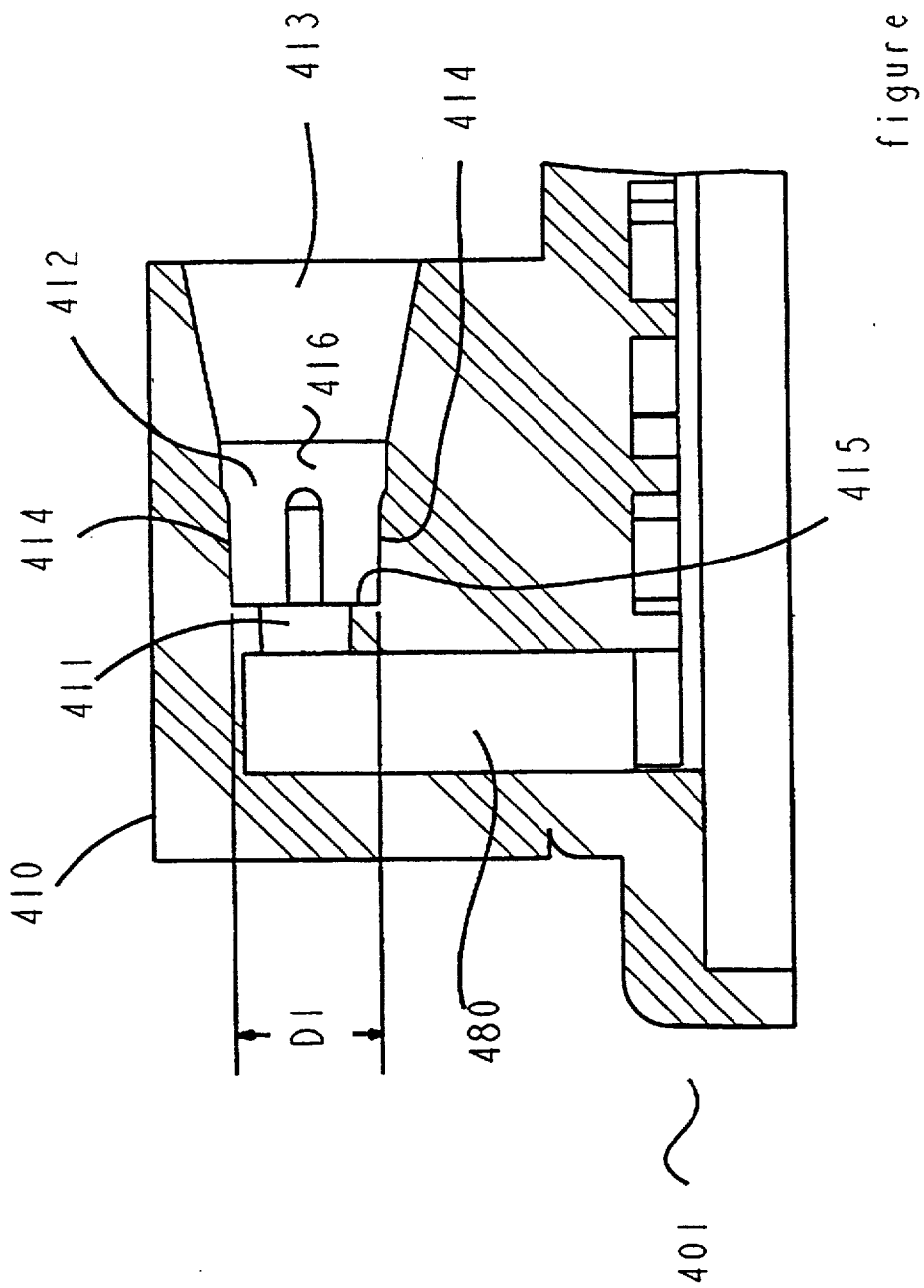
FIG. 24 depicts a sectional representation from the side of the right angle port assembly of FIG. 23.

Referring to FIGS. 19, 23 and 24, tube socket 416 contains tapered hole 413 and tapered hole 412. The walls of tapered hole 412 contain protruding ribs 414. The tube socket 416 illustrated contains four protruding ribs 414. However, more than four ribs or less than four ribs could be used. A UV curable adhesive 420 (FIG. 19) may be used to bond inlet tube 417 to tube socket 416. However, other adhesives may also be used. In order to bond the tube 417, tube 417 is inserted into tube socket 416 dry. The smallest diameter of tapered hole 412 is made large enough so that inlet tube 417 can be easily inserted into tapered hole 412. The four ribs 414 protrude deep enough into tapered hold 412 to assure firm contact with tube 417 in order to hold tube 417 in place before the adhesive is applied. Tapered hole 412 should also have sufficient taper to allow the tube socket to be easily molded. Also, the taper on tapered hole 413 should be sized to provide a large enough gap between the inside of tapered hole 413 and the outside of inlet tube 417 to allow the UV curable adhesive 420 to be injected into the gap. A relatively high viscosity UV curable adhesive 420 should be used to assure that the UV curable adhesive 420 cannot flow through the gap between the outside of inlet tube 417 and the inside of tapered hole 412 and then into port 411 while the UV curable adhesive 420 is in the uncured state. If the gap 419 between right angle port assembly 410 and tube guide 430 is too small to allow the injection of UV curable adhesive 420 into the gap around inlet tube 417, from gap 419, then a small hole can be molded into the top of right angle port assembly 410 near the maximum diameter end of tapered hole 413. The UV curable adhesive 420 could then be injected through this hole into the gap around inlet tube 417.

Figure 25:
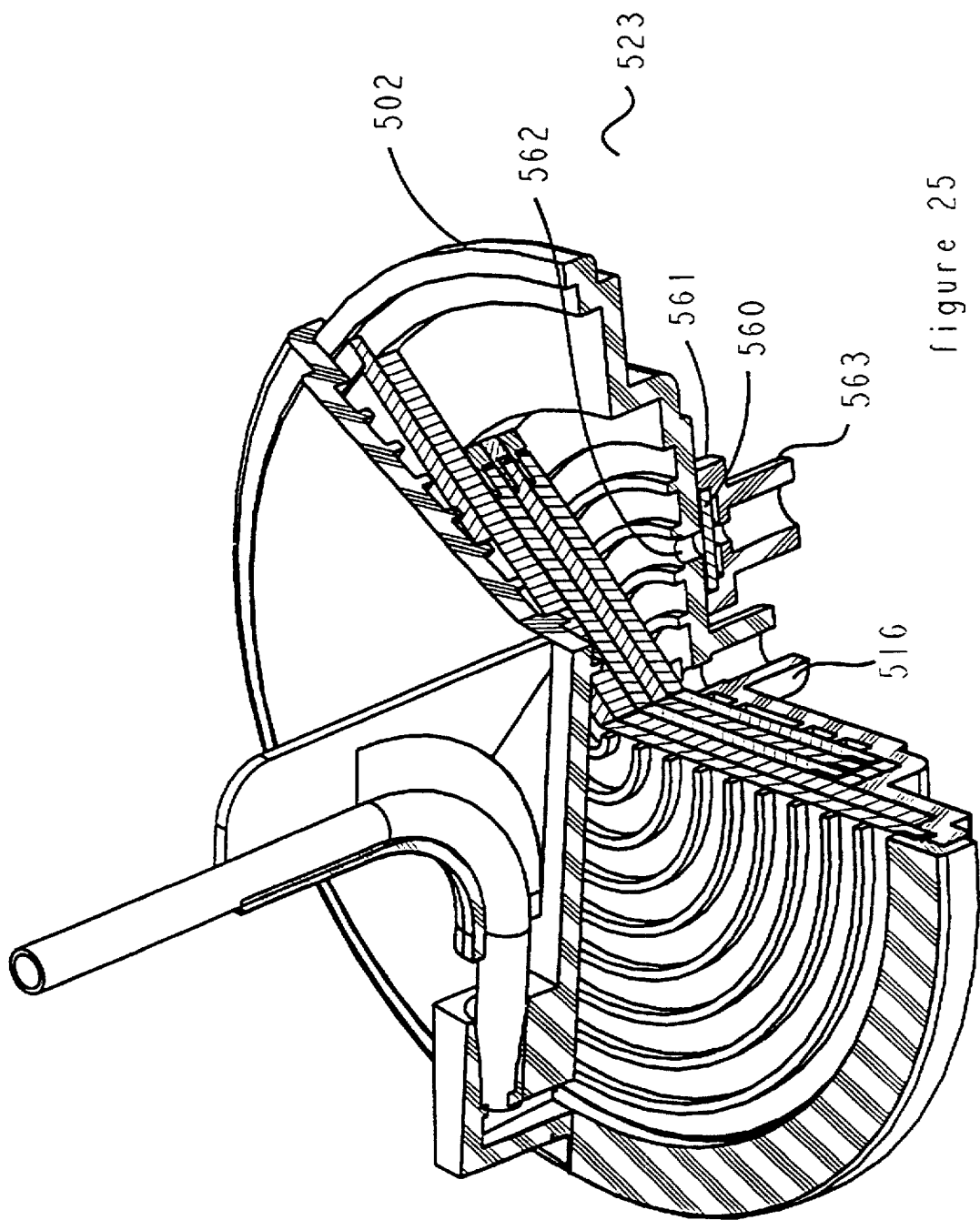
FIG. 25 depicts a sectional isometric view with portions removed therefrom of the filtration device of FIGS. 17–21 further including a hydrophilic vent filter affixed thereto and in direct communication with a modified spiral channel in the outlet section of the filtration device to allow air to vent therefrom.

A further embodiment of the filtration device constructed in accordance with the principles of the present invention is illustrated in FIG. 25. This filtration device 523 is identical to the filtration device 423 depicted in FIG. 17 but also includes a vent port 562 and hydrophilic filter 560 within a hydrophilic vent device 561 affixed to outlet section 502. Outlet section 502 is identical to outlet section 302 of the device in FIG. 17 with the exception that the outlet section 502 contains vent port 562.

Figure 27:
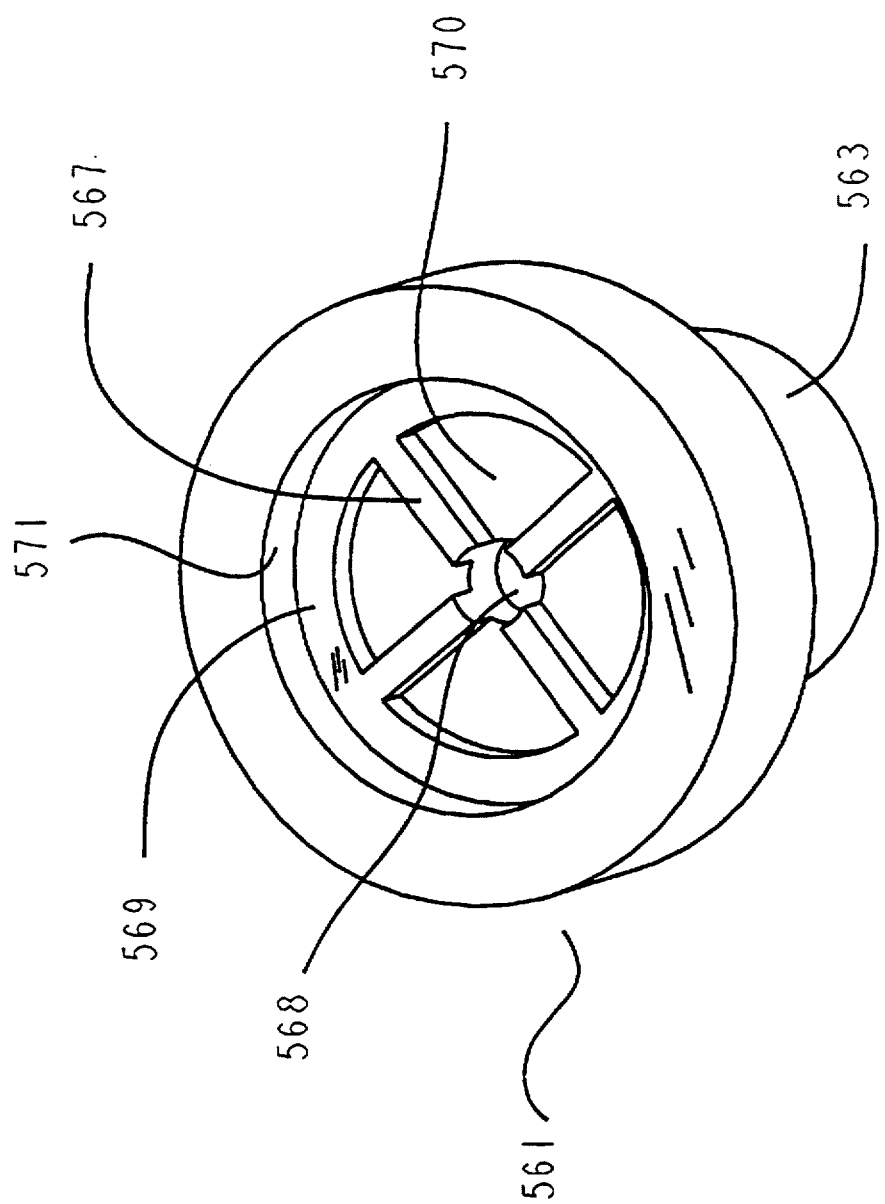
FIG. 27 depicts an isometric view of the housing of the hydrophilic vent filter of the filtration device depicted in FIG. 25.

Referring to FIG. 27, the hydrophilic vent device 561 contains filter support ribs 567, outlet port 568, filter sealing surface 569, side wall 571, tube socket 563 and downstream chamber 570. The filter sealing surface 569 forms a lip within the vent device 561. Filter support ribs 567 extend radially inward from filter sealing surface 569 to the center of the filter housing forming outlet port 568. Hydrophilic filter 560 (FIG. 25) is inserted into the well formed by side wall 571 and sealing surface 569 and sealed to sealing surface 569. The seal may be formed by using a heat seal, an ultrasonic seal or a glue seal. Alternatively outlet section 502 could contain a set of filter support ribs and a filter sealing surface. The filter support ribs and filter sealing surface on outlet section 502 could be a mirror image of those on vent device 561. The hydrophilic filter 560 could be sealed between the filter sealing surface 569 of hydrophilic vent device and the sealing surface of outlet section 502 using a compression seal. Hydrophilic vent device 561 is bonded to outlet section 502 in a leak tight manner. This bond could be formed by an ultrasonic bond, a heat bond, a glue bond, a solvent bond or any other type of leak tight bond.

Figure 26:
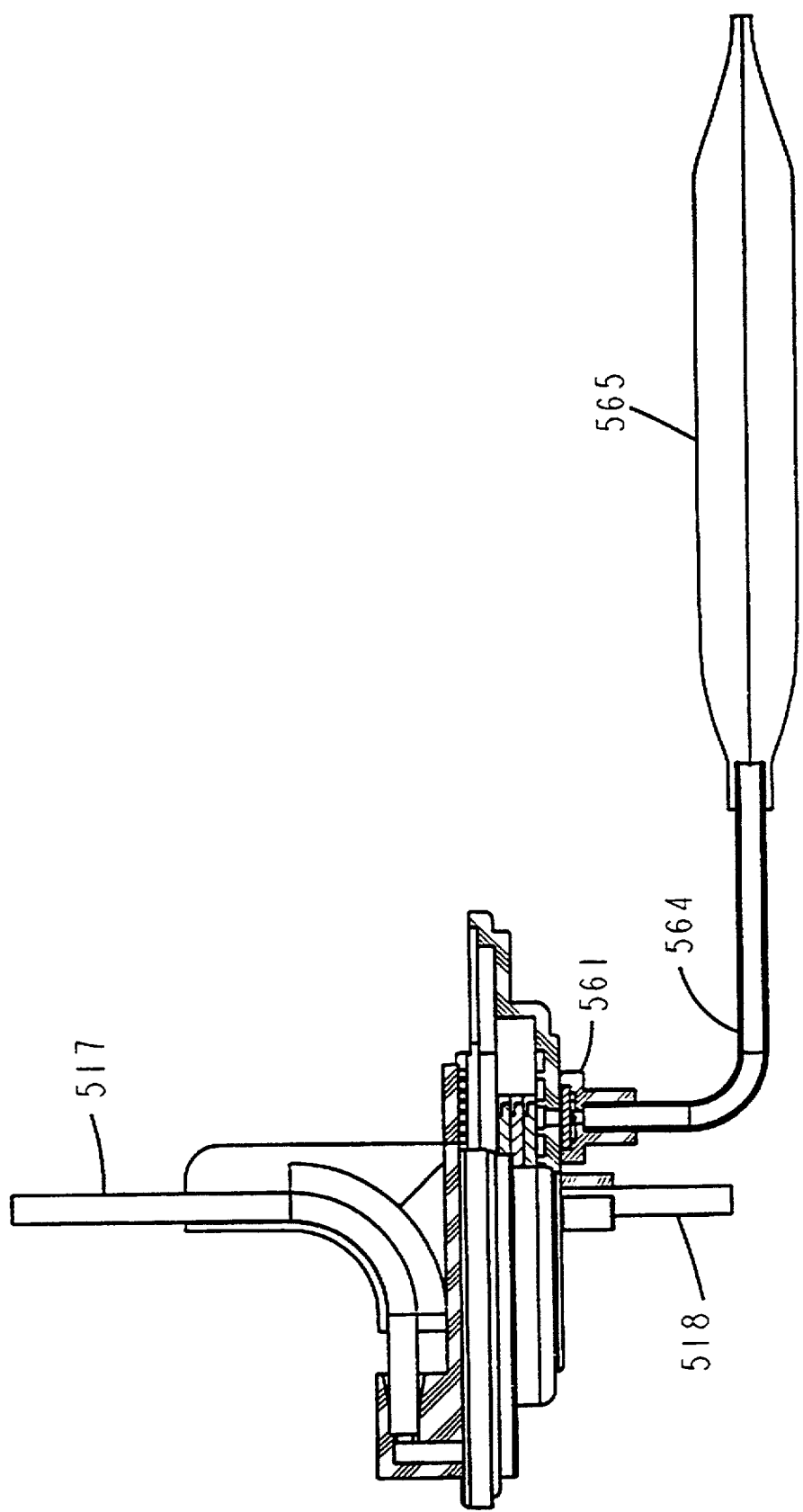
FIG. 26 depicts a sectional schematic representation of the filtration device of FIG. 28 having an air collection bag and tubing attached to the hydrophilic vent filter in order to collect air from the filtration device in the air collection bag.

The filtration device 523 is used in the same manner as previously discussed in reference to the embodiments of the filtration device 23 shown in FIGS. 1 and 2, and is placed in operational assembly in a similar manner. However, an additional tube leading to an air recovery bag is attached to the vent device 561. FIG. 26 depicts filtration device 523 as depicted in FIG. 25 including inlet tube 517, outlet tube 518 and air bag 565. When filtering blood in an operational assembly, inlet tube 517 (near the inlet end of inlet tube 517) is closed using a tube clamp (not illustrated). Outlet tube 518 would also be closed with a tube clamp (not illustrated) close to tube socket 563 of outlet half 502. Then a sterile connection between the inlet end of inlet tube 517 and the feed blood bag (not shown) is made using a sterile docking device as is well known in the art. The actual sterile connection is made between inlet tube 517 and a short length of tube which is a part of a feed blood bag. The feed blood bag (not shown) may be suspended from an appropriate mechanism such as pole with hook (not shown). Air bag 565 could also be suspended from the pole or it could hang from the filtration device 523 or it may rest on a surface such as bench top or the like. Similarly, the receiving blood bag (not shown) may be suspended or may rest on a surface such as a bench top or the like.

Referring to FIGS. 25 and 26, once the tubing clamp (not shown) on inlet tube 517 is opened, blood will begin to flow from a feed blood bag through inlet tube 517, through port 480, into outermost concentric circular channel 489. Filter elements 303, 304, 305 and 306 will wet as described supra with regard to filtration device 423 depicted in FIG. 17. The air that is purged from inlet tube 517 and from the interior of air bag device 523 will flow through port 562, then through hydrophilic filter 561, through air bag tube 564 into air bag 565. Because the air bag device 523 with the air bag tube 564 and the air bag 565 comprise a sealed system, it is not necessary that hydrophilic filter 560 be a sterilizing grade filter. As blood starts to flow from filter element 306, the lower modified spiral channel in the outlet section 502 will begin to fill with blood. When the blood in the lower modified spiral channel reaches port 562 hydrophilic filter 560 will wet and the blood will immediately clog hydrophilic filter 560. Hence blood will not be able to flow into air bag tube 564 and then into air bag 565 (FIG. 26). Thus hydrophilic filter 560 acts as a valve that allows air to flow through it until it becomes wet. Because outlet tube 518 is closed by a tube clamp (not illustrated) blood flow will now stop. The tube clamp on outlet tube 518 may now be opened and blood flow will resume and the small amount of air that is left in air bag device 523 along with any air that is in outlet tube 518 will be purged into the receiving blood bag. Blood will then flow from air bag device 523 through outlet tube 518 into the receiving blood bag. If desired, hydrophilic filter 560 may be observed through a transparent hydrophilic vent device 561 to see if it has been wet before opening the tube clamp on outlet tube 518. Alternatively, the user can wait for a minimum time period (known from experience or determined by instructions from the manufacturer).

Figure 31:
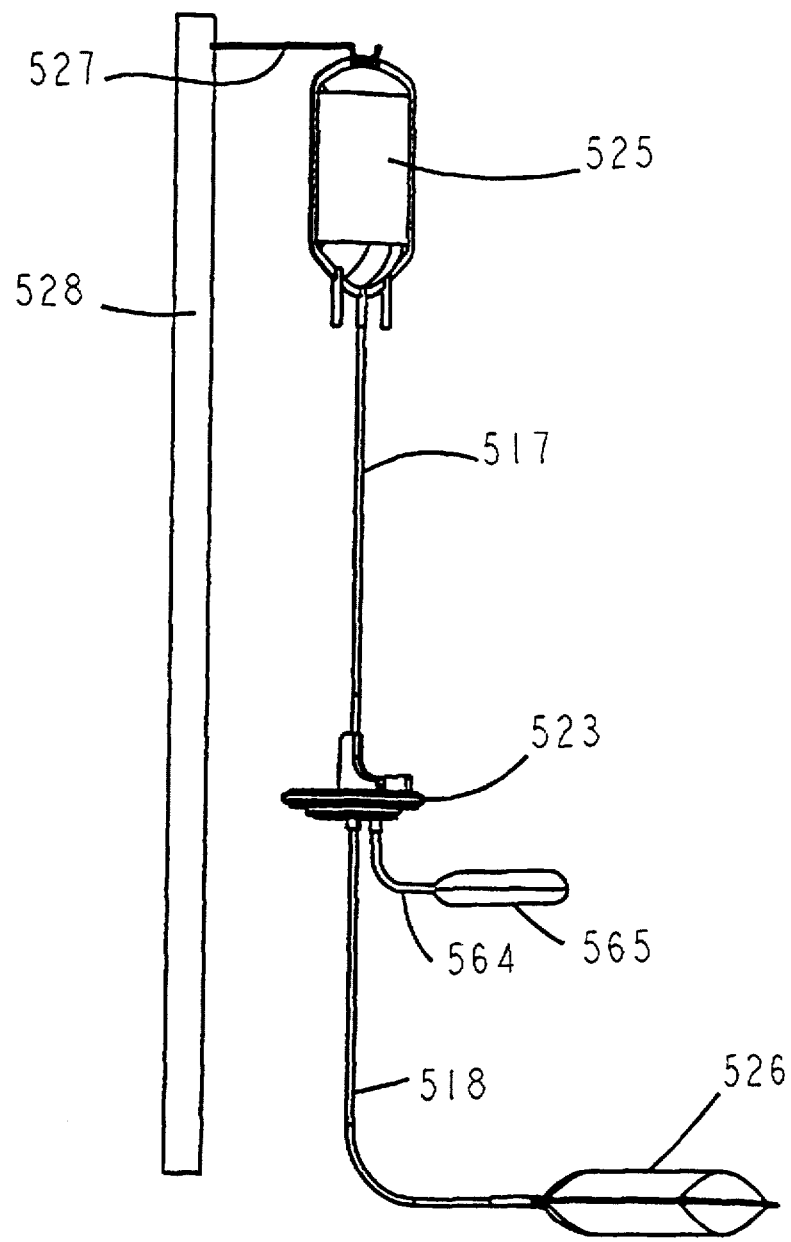
FIGS. 31 and 33 depict the filtration device of FIGS. 17-21 in operational assembly with the hydrophilic vent filter along with an air receiving bag, blood receiving bag, and blood supply bag.

From the above description, it can be seen that filtration device 523 maintains all of the advantages of filtration device 423 depicted in FIG. 17 and also reduces the amount of air in the receiving blood bag. Once the filtration system is set up as illustrated in FIG. 31, the filtration process begins by opening the tube clamp (not shown) on inlet tube 517. At any time after the air bag device 523 and hydrophilic filter 560 have wet, the user need only open the tube clamp on outlet tube 518 to complete the filtration process. Once the filtration process is complete, the user may seal the outlet tube 518 (which will be full of blood) and then cutaway and discard in a safe manner air bag filtration device 523 which will have attached to it, inlet tube 517, a feed blood bag, air bag tube 564 and air bag 565. The receiving blood bag which will have outlet tube 518 attached to it, can then be stored.

Figure 28:
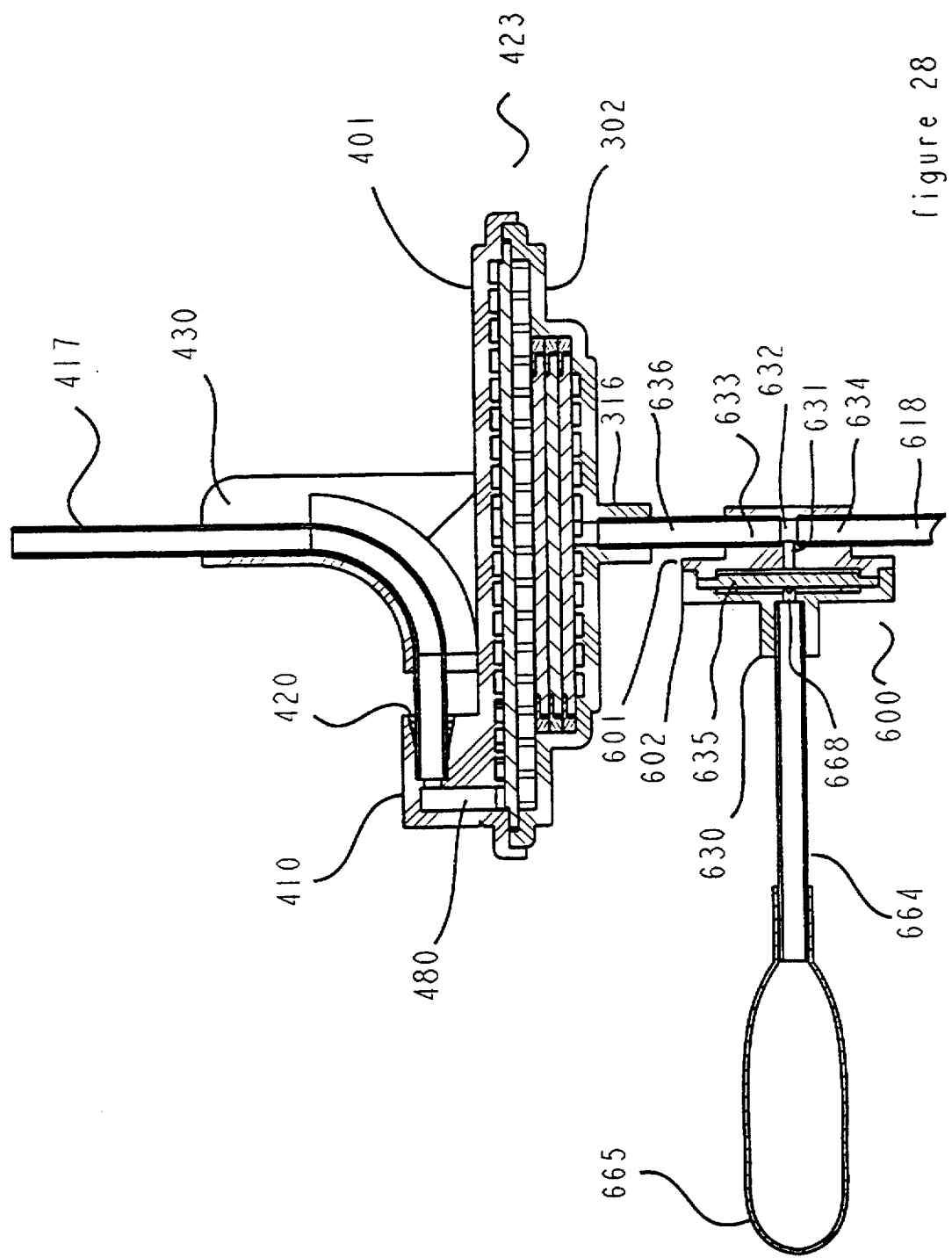
FIG. 28 depicts a sectional view of the filtration device of FIGS. 19–21 having an in-line hydrophilic vent filter connected to the outlet port thereof with tubing to allow air to vent from the filtration device therethrough.
Figure 29:
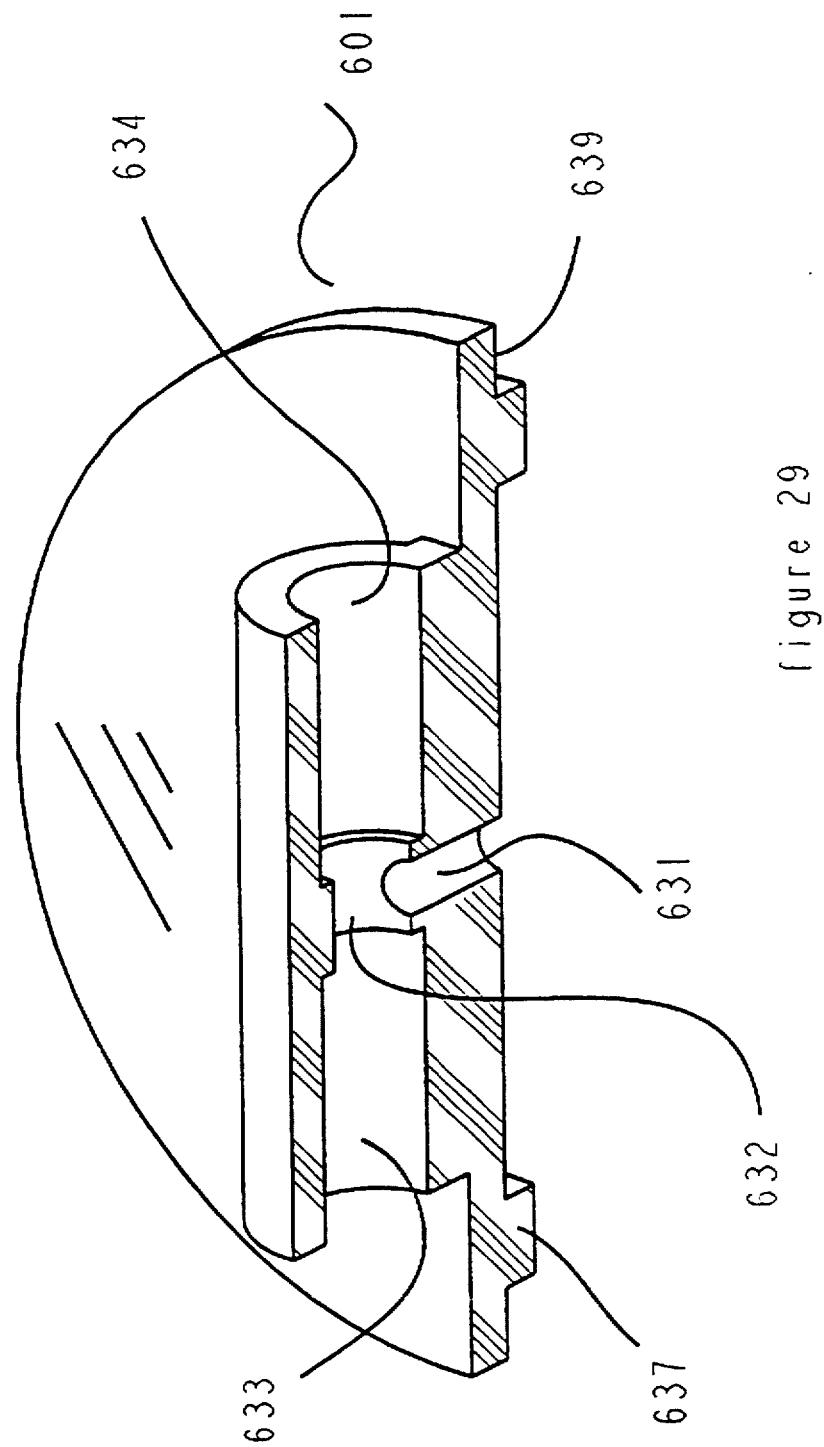
FIG. 29 depicts an isometric sectional view of the inlet section of the hydrophilic vent filter having portions removed therefrom constructed in accordance with the present invention.

A further embodiment of the filtration device illustrated in FIG. 25 is shown in FIG. 28 and includes a hydrophilic vent device 600 connected inline between tube 636 and outlet tube 618. Referring to FIGS. 28 and 29, inlet section 601 of the hydrophilic vent device 600 contains inlet tube socket 633 and outlet tube socket 634. Inlet tube socket 633 is in fluid flow relationship with outlet tube socket 634 through a port 632. Inlet chamber 630 is in fluid flow relationship with port 632 through another port 631. Hence inlet chamber 630 is in fluid flow relationship with tube 636 and outlet tube 618 and tube 636 communicates with outlet tube 618 through port 632 (FIG. 28). Inlet half 601 also contains filter sealing rib 637 protruding axially therefrom.

Figure 30:
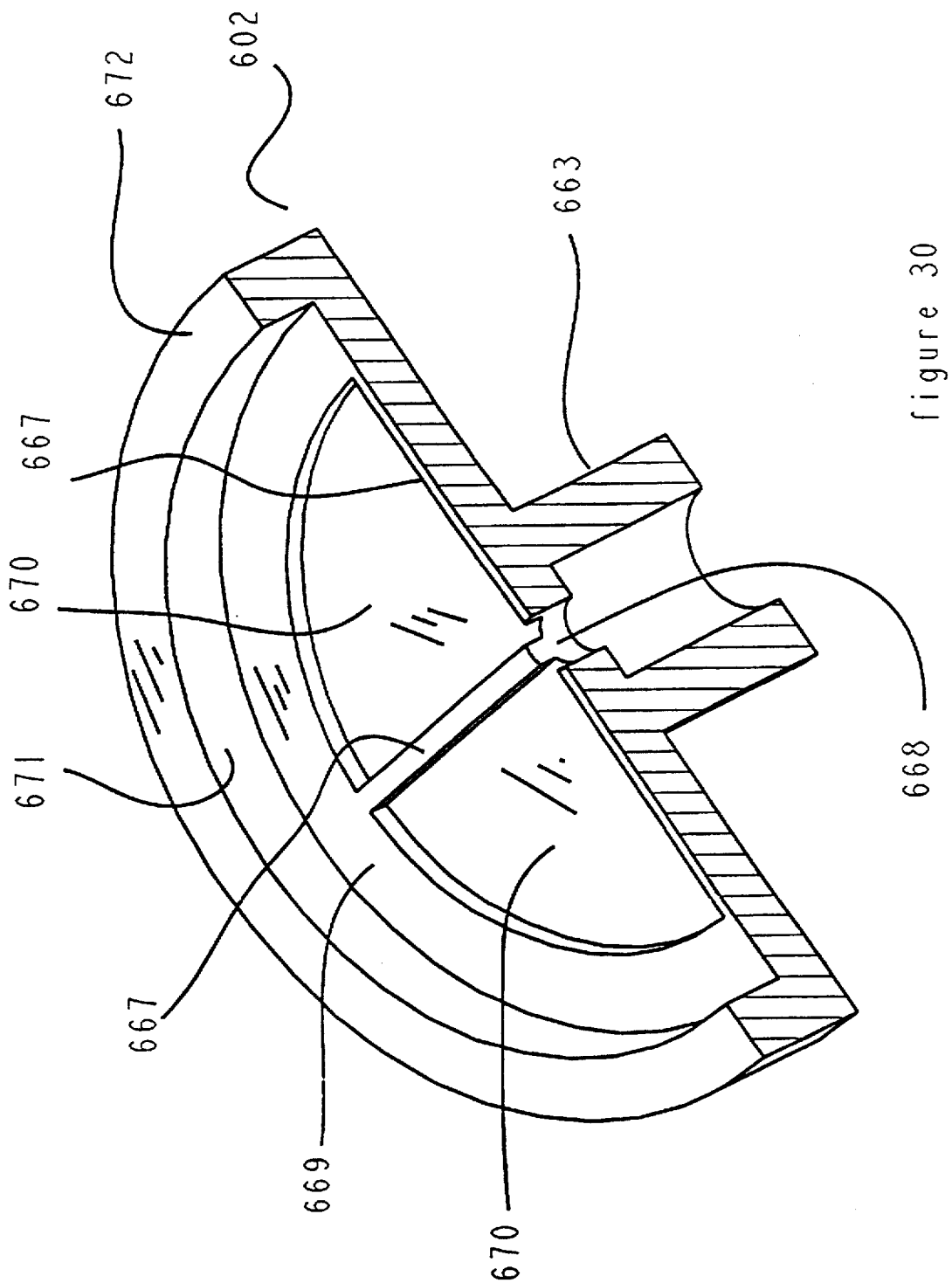
FIG. 30 depicts an isometric sectional view of the outlet section of the hydrophilic vent filter having portions removed therefrom constructed in accordance with the present invention.
Figure 32:
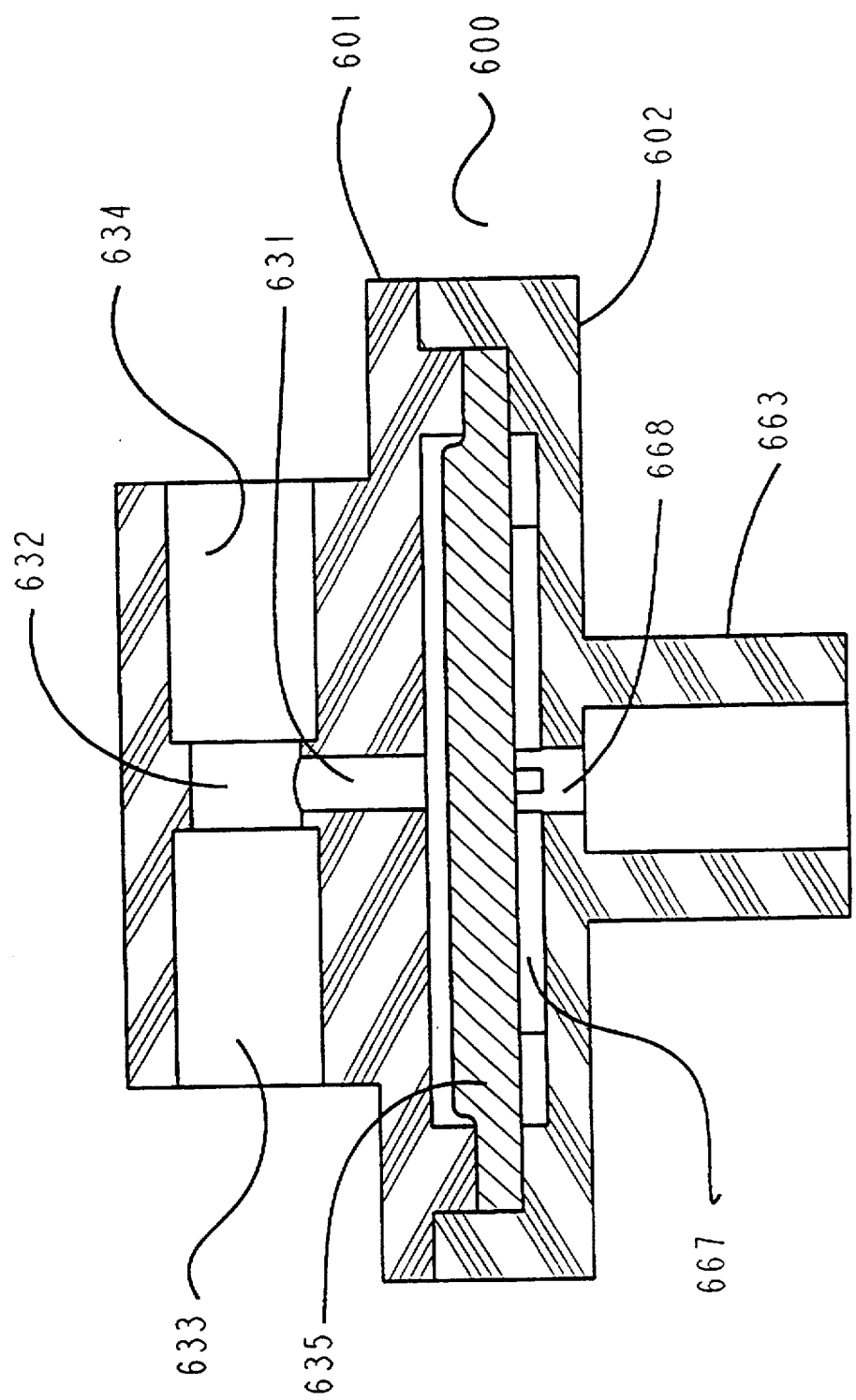
FIG. 32 depicts a sectional representation from the side of the hydrophilic filter element depicted in FIG. 28.

Referring to FIGS. 30 and 32, outlet section 602 of hydrophilic filter device 600 contains filter support ribs 667, outlet port 668, filter sealing surface 669, side wall 671, tube socket 663 and downstream chamber 670. Hydrophilic filter 635 (FIG. 32) is inserted into the well formed by side wall 671 and sealing surface 669. Hydrophilic filter 635 is sealed into hydrophilic vent device 600 using a compression seal formed by the outer periphery of hydrophilic filter 635 being compressed between filter sealing surface 669 of outlet section 602 and filter sealing rib 637 of inlet section 601. Hydrophilic filter 635 could however be sealed to outlet half 602 by a heat seal, an ultrasonic seal, a glue seal, a solvent seal or by any other type of seal.

Figure 33:
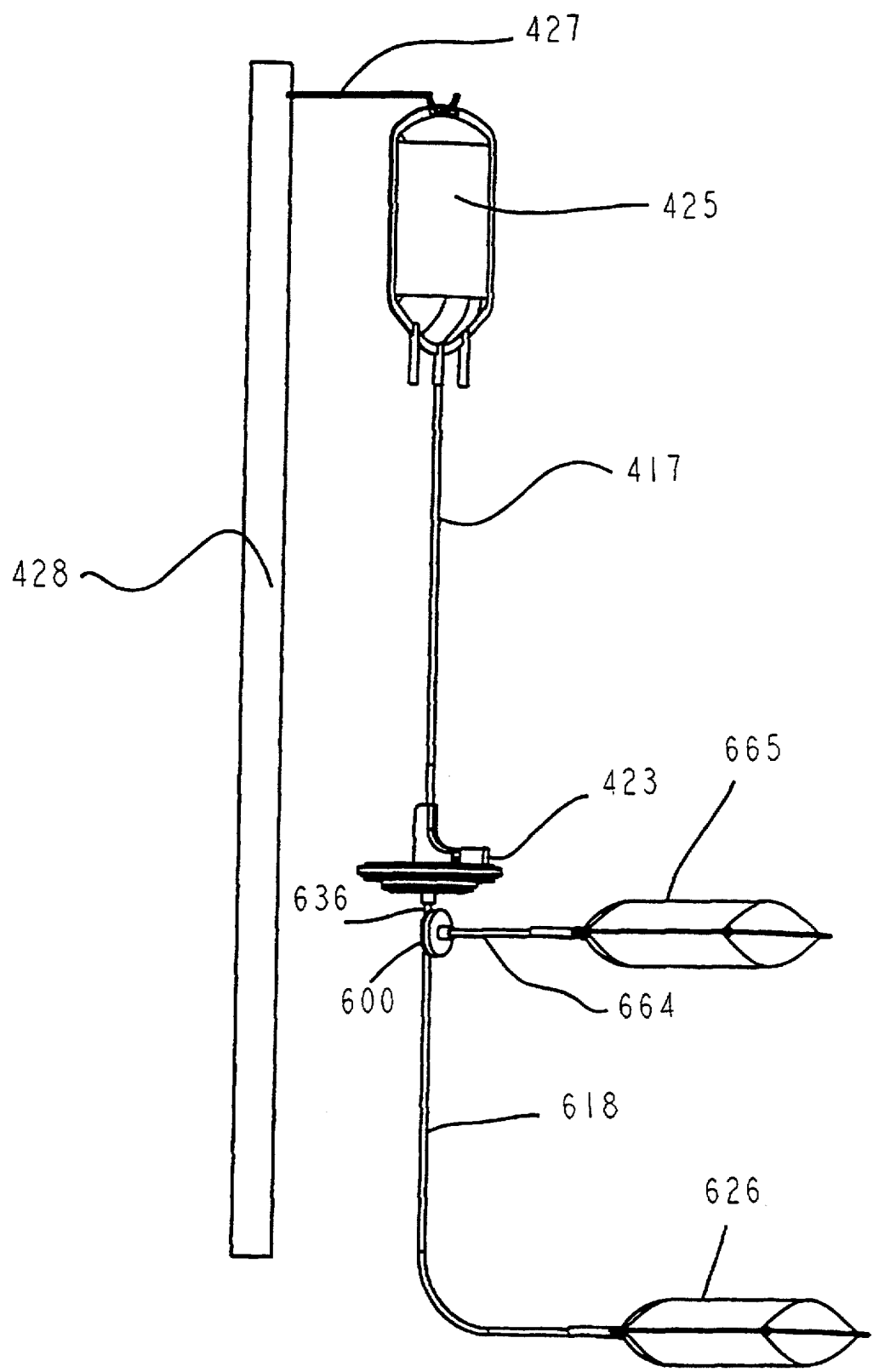

FIG. 33 depicts the filtration device 423 of FIG. 17 and hydrophilic vent device 600 of FIG. 32 in an operational assembly with inlet tube 417, outlet tube 618, feed blood bag 425, tube 636, receiving blood bag 626, air bag tube 664 and air bag 665.

When filtering blood, inlet tube 417 would first be closed (near the inlet end of inlet tube 417) with a tube clamp (not illustrated). Outlet tube 618 would also be closed with a tube clamp (not illustrated) near to tube socket 634 of hydrophilic vent device 600. Then a sterile connection between the inlet end of inlet tube 417 and the feed blood bag 425 is made using a sterile docking device as is well known in the art. The actual sterile connection is made between inlet tube 417 and a short length of tube which is part of feed blood bag 425. Feed blood bag 425 may be suspended from an appropriate mechanism such as pole 428 with hook 427. Air bag 665 could be suspended from pole 428 or it could rest on a surface such as a bench top or the like. The receiving blood bag 626 may be suspended by the mechanism or may rest on a surface such as bench top or the like.

Referring to FIGS. 28 and 33, once the tube clamp on inlet tube 417 (not shown) is opened, blood will begin to flow from feed blood bag 425 through inlet tube 417, through port 480, into outermost concentric circular channel 489. Filter elements 303, 304, 305 and 306 will wet the same as they did in the filtration device 423 shown in FIG. 17. The air that is purged from inlet tube 417 and from the interior of filtration device 423 will flow out of filtration device 423 through tube 636, through port 632, through port 631, through hydrophilic filter 635, through air bag tube 664 into air bag 665. Because the midstream screen device 423 with tube 636 and hydrophilic vent device 600 and air bag tube 664 and air bag 665 and outlet tube 618 and receiving blood bag 626 comprise a sealed system it is not necessary that hydrophilic filter be a sterilizing grade filter. Once filtration device 423 is wet with blood, blood will begin to flow from outlet port 316 into tube 636. Because outlet tube 618 is closed with a tube clamp (not shown) the blood will flow from tube 636 through port 632 and then through port 631 into upstream chamber 630 of hydrophilic vent device 600. The blood in upstream chamber 630 will wet hydrophilic filter 635. Once wet, air will no longer be able to flow through hydrophilic filter 635. The pore size of hydrophilic filter 635 should be made small enough so that the blood will immediately clog hydrophilic filter 635. Hence, blood will not be able to flow into air bag tube 664 and then into air bag 665 and hydrophilic filter 635 acts as a valve that allows air to flow through it until it becomes wet. Once wet with blood hydrophilic filter acts as a valve that is closed to both air flow and to blood flow. Because outlet tube 618 is closed by a tube clamp (not illustrated), blood flow will now stop. The user may now open the tube clamp on outlet tube 618. At this time, blood flow will resume and the air that is in outlet tube 618 will be purged into receiving blood bag 626. Blood will then flow from filtration device 423, through tube 636, through port 632, through outlet tube 618 into receiving blood bag 626. The user can observe hydrophilic filter 635 (through a transparent housing) to see if it has been wet before opening the tube clamp on outlet tube 618 or the user can wait for a minimum time period (known from experience or determined by instructions from the manufacturer).

From the above description, it can be seen that filtration device 423 combined with hydrophilic vent device 600 maintains all of the advantages of midstream screen device 423 and also reduces the amount of air in receiving blood bag 526. Once the filtration system is set up as illustrated in FIG. 33, the user will begin the filtration process by opening the tube clamp (not shown) on inlet tube 417. At any time after filtration device 423 and hydrophilic vent device 600 have wet, the user need only open the tube clamp on outlet tube 618 to complete the filtration process. Once the filtration process is complete the user will seal the outlet tube 618 (which will be full of blood) and then cutaway and discard in a safe manner midstream screen device 423 which will have attached to it, inlet tube 417, feed blood bag 425, tube 636, hydrophilic vent device 600, air bag tube 664 and air bag 665. The receiving blood bag 626 which will have outlet tube 618 attached to it, can then be stored.

Although the invention has been described with reference to the embodiment depicted herein. It will be apparent to one of ordinary skill in the art that various modifications to embodiments may be made without departing from the scope of the invention as defined by the following claims.

What is claimed is:

1. A blood or blood product filtration device comprising:
    a housing having an inlet port and outlet port therein;
    at least one blood or blood product filter element disposed within the housing between the inlet port and outlet port and dividing the housing into a first chamber and second chamber, said at least one filter element being sealed to said housing to prevent liquid from flowing in between the filter element and the housing;
    a flow deflector disposed within said first chamber between said filter elements and the inlet port, said flow deflector being adapted to direct the flow of blood or blood product being filtered to substantially the outer edge of said at least one filter element and being spaced from said at least one filter element a distance wherein air trapped therebetween is forced through said at least one filter element by said blood or blood product into said second chamber;
    a first channel disposed below said filter element in said second chamber, said first channel adapted to allow fluid to flow to the outlet port from the filter element;
    a second channel, said second channel being within said first chamber and adapted to allow fluid to flow to the filter element wherein said second channel comprises a spiral channel, leading from an outer periphery of the first chamber to a central location within the first chamber; and
    a third channel extending radially outward from the inlet port to the second channel.

2. The filtration device of claim 1 further comprising more than one filter element wherein a seal ring is mounted between two of said filter elements.

3. The filtration device of claim 2 wherein said inlet port and outlet port are coaxially oriented.

4. The filtration device of claim 2 wherein said housing comprises an inlet section and an outlet section attached to said inlet section, said inlet port being disposed within said inlet section and said outlet port being disposed within said outlet section.

5. The filtration device of claim 4 wherein said filter element is sealed between said inlet section and one of the outlet section and a seal ring.

6. The filtration device of claim 4 comprising a plurality of filter elements, said filter elements being stacked atop of one another and being separated about their periphery by a seal ring.

7. The filtration device of claim 1 wherein said flow deflector comprises a disk.

8. The filtration device of claim 7 wherein said disk is suspended in said first chamber.

9. The filtration device of claim 1 further comprising more than one filter element wherein a seal ring is mounted between two of said filter elements.

10. The filtration device of claim 1 wherein said inlet port and outlet port are coaxially oriented.

11. The filtration device of claim 1 wherein said filtration device comprises an inlet section and an outlet section, said inlet port being disposed within said inlet section and said outlet port being disposed within said outlet section.

12. The filtration device of claim 11 wherein said filter element is sealed between said inlet section and the outlet section.

13. The filtration device of claim 1 further comprising a plurality of filter elements, said filter elements being stacked atop one another and being separated about their periphery by a sealing ring.

14. The filtration device of claim 1 wherein said first channel comprises a substantially spiral channel.

15. The filtration device of claim 1 wherein said filter element covers said first channel whereby liquid filtered with said filter element flows directly into said first channel.

16. The filtration device of claim 1 wherein said second channel covers the filter element wherein liquid within said second channel flows directly into said filter element.

17. The filtration device of claim 16 wherein said inlet port is located about a periphery of the housing and said second channel extends from a periphery of the first chamber to a central location within the first chamber.

18. The filtration device of claim 17 wherein the inlet port is adapted to receive flexible tube therein and comprises a tapered hole.

19. The filtration device of claim 18 further comprising a tube guide on said housing adapted to guide a flexible tube into said inlet port.

20. The filtration device of claim 19 wherein said tube guide on said housing further comprises a substantially right angle support member.

21. The filtration device of claim 18 further comprising at least one protruding rib extending from an inside diameter of said hole.

22. The filtration device of claim 1 wherein said second channel comprises a modified spiral channel wherein of the radially outermost edges of the channel align with the outermost edges of the effective filtration area of the filter element.

23. The filtration device of claim 1 further comprising means for supporting said filter element within said filtration device.

24. The filtration device of claim 23 wherein said supporting means comprises a screen.

25. The filtration device of claim 1 further comprising a second outlet port, said second outlet port being positioned within said housing at a location downstream of said at least one filter element to allow air within the housing to flow therethrough and out of said housing, said second outlet port having a hydrophilic filter disposed to allow air to pass through said second outlet port without allowing certain liquids to flow therethrough.

26. The filtration device of claim 1 further comprising an in-line vent device in fluid flow relationship with said outlet port, said in-line vent device being adapted with a hydrophilic filter therein, an inlet, a first outlet and a second outlet, said hydrophilic filter being located between the inlet and the first outlet and adapted to allow air to pass therethrough without allowing certain liquids to pass therethrough.

27. The filtration device of claim 1 wherein the distance between the flow deflector and the inlet port prevents gases within the housing from accumulating within the first chamber when liquid flows into the first chamber via the inlet port.

* * * * *